(12) United States Patent
Nazarian et al.

(10) Patent No.: US 12,352,454 B2
(45) Date of Patent: Jul. 8, 2025

(54) PORTABLE TEMPERATURE CONTROLLED DEVICE

(71) Applicant: Therabody, Inc., Los Angeles, CA (US)

(72) Inventors: Benjamin Nazarian, Los Angeles, CA (US); Jaime Sanchez Solana, Los Angeles, CA (US); Washington Alexander Silva Garces, Los Angeles, CA (US); Alex Zhu, Xiamen (CN); Kevin Xie, Los Angeles, CA (US); Jamie Dachisen, Los Angeles, CA (US)

(73) Assignee: Therabody, Inc., Los Angeles, CA (US)

( * ) Notice: Subject to any disclaimer, the term of this patent is extended or adjusted under 35 U.S.C. 154(b) by 0 days.

(21) Appl. No.: 18/816,707

(22) Filed: Aug. 27, 2024

(65) Prior Publication Data

US 2025/0043966 A1 Feb. 6, 2025

Related U.S. Application Data

(63) Continuation of application No. PCT/CN2024/108734, filed on Jul. 31, 2024, which is
(Continued)

(51) Int. Cl.
*F24F 1/04* (2011.01)
*F24F 5/00* (2006.01)
*F24F 11/63* (2018.01)

(52) U.S. Cl.
CPC .............. *F24F 1/04* (2013.01); *F24F 5/0042* (2013.01); *F24F 11/63* (2018.01)

(58) Field of Classification Search
CPC . F24F 1/04; F24F 11/63; F24F 5/0042; F25D 31/007; F25D 11/003; F25D 3/08;
(Continued)

(56) References Cited

U.S. PATENT DOCUMENTS

| 1,545,027 A | 7/1925 | Ashlock |
| D143,678 S | 1/1946 | Snyder et al. |

(Continued)

FOREIGN PATENT DOCUMENTS

| CN | 104507426 A | 4/2015 |
| CN | 104984624 A * | 10/2015 |

(Continued)

OTHER PUBLICATIONS

International Search Report and Written Opinion of the International Searching Authority, directed to related International Patent Application No. PCT/CN2024/108734, mailed Nov. 12, 2024, 10 pages.

*Primary Examiner* — Nelson J Nieves
(74) *Attorney, Agent, or Firm* — Sterne, Kessler, Goldstein & Fox P.L.L.C.

(57) ABSTRACT

A hand-held portable temperature-controlled device includes a cylindrical housing comprising an air inlet and an air outlet in fluid communication with each other. A fan can be located within the cylindrical housing, and a heat sink can be disposed adjacent to the fan. The hand-held portable temperature-controlled device can also include a controllable temperature element configured to generate heating and cooling. The hand-held portable temperature-controlled device can also include a heat spreader disposed adjacent to the controllable temperature element and configured to contact a face of a user. A top surface of the heat spreader can be oriented at a non-zero angle relative to a bottom surface of the heat spreader.

24 Claims, 26 Drawing Sheets

Related U.S. Application Data a continuation of application No. 18/425,382, filed on Jan. 29, 2024, which is a continuation of application No. 18/362,349, filed on Jul. 31, 2023, now Pat. No. 11,940,163.

(58) Field of Classification Search
CPC ............... F25D 2400/12; F25D 29/003; F25D 2331/805; F25D 2331/803; F25B 21/02; A61F 2007/0075

See application file for complete search history.

(56) References Cited

U.S. PATENT DOCUMENTS

| | | | |
|---|---|---|---|
| 2,987,334 A | 6/1961 | Wendling | |
| 3,705,579 A | 12/1972 | Morini et al. | |
| D230,522 S | 2/1974 | Norman | |
| 3,971,229 A * | 7/1976 | Privas | A61F 7/00 |
| | | | 62/3.62 |
| 4,046,142 A | 9/1977 | Whitney | |
| D265,002 S | 6/1982 | Hubner | |
| 4,976,706 A | 12/1990 | Aki et al. | |
| 5,014,681 A | 5/1991 | Heeman et al. | |
| 5,092,317 A | 3/1992 | Zelikovski | |
| 5,103,809 A | 4/1992 | DeLuca et al. | |
| D353,205 S | 12/1994 | Canavan | |
| D417,284 S | 11/1999 | Kondo | |
| 6,093,164 A | 7/2000 | Davis et al. | |
| D439,984 S | 4/2001 | Thach | |
| 6,406,445 B1 | 6/2002 | Ben-Nun | |
| 6,558,338 B1 | 5/2003 | Wasserman | |
| 6,567,696 B2 * | 5/2003 | Voznesensky | A61N 1/36021 |
| | | | 607/108 |
| 6,591,142 B1 | 7/2003 | Dea | |
| D479,877 S | 9/2003 | Lee et al. | |
| 6,823,762 B2 | 11/2004 | Hu | |
| 6,846,295 B1 | 1/2005 | Ben-Nun | |
| D518,895 S | 4/2006 | Weaver, II et al. | |
| 7,022,093 B2 | 4/2006 | Smith et al. | |
| 7,207,953 B1 | 4/2007 | Goicaj | |
| D554,268 S | 10/2007 | Harding | |
| D554,761 S | 11/2007 | Marin | |
| D571,923 S | 6/2008 | Roberts | |
| 7,431,706 B2 | 10/2008 | Louis | |
| D582,047 S | 12/2008 | Yim | |
| 7,509,692 B2 | 3/2009 | Elkins et al. | |
| D598,556 S | 8/2009 | Chen | |
| D608,006 S | 1/2010 | Avitable et al. | |
| D613,870 S | 4/2010 | Shust | |
| D635,682 S | 4/2011 | Chiang | |
| 7,927,259 B1 | 4/2011 | Rix | |
| 7,927,294 B2 | 4/2011 | Kamimura et al. | |
| D638,948 S | 5/2011 | Janzon | |
| D659,644 S | 5/2012 | Gretz | |
| 8,313,450 B2 | 11/2012 | Ben-Nun | |
| D678,531 S | 3/2013 | Patil | |
| D695,902 S | 12/2013 | Daniels et al. | |
| 8,622,943 B2 | 1/2014 | Ben-Nun | |
| D704,848 S | 5/2014 | Thomas et al. | |
| 8,764,688 B1 | 7/2014 | Nauman et al. | |
| 8,777,881 B2 | 7/2014 | Tsai | |
| D712,052 S | 8/2014 | Thomas et al. | |
| D716,457 S | 10/2014 | Brefka et al. | |
| 9,017,273 B2 | 4/2015 | Burbank et al. | |
| D735,873 S | 8/2015 | Brefka et al. | |
| 9,125,442 B2 | 9/2015 | Brown | |
| D751,720 S | 3/2016 | Williams | |
| D754,355 S | 4/2016 | Ganapathy et al. | |
| D756,180 S | 5/2016 | Chen | |
| D762,869 S | 8/2016 | Beckman et al. | |
| D764,672 S | 8/2016 | Vosch et al. | |
| 9,414,954 B2 | 8/2016 | Brown | |
| 9,549,870 B2 | 1/2017 | Shafieloo | |
| D786,447 S | 5/2017 | Bigelow et al. | |
| D800,326 S | 10/2017 | Cox | |
| 9,849,024 B2 | 12/2017 | Mandel | |
| D806,888 S | 1/2018 | Cheng et al. | |
| D810,311 S | 2/2018 | Chen | |
| D811,613 S | 2/2018 | Marton et al. | |
| D811,614 S | 2/2018 | Marton et al. | |
| 9,889,066 B2 | 2/2018 | Danby et al. | |
| 9,901,510 B2 | 2/2018 | Smith | |
| D817,732 S | 5/2018 | Rettler | |
| D820,994 S | 6/2018 | Trapp | |
| D822,221 S | 7/2018 | Huth et al. | |
| D831,221 S | 10/2018 | Smith | |
| 10,123,937 B2 | 11/2018 | Pisharodi et al. | |
| 10,159,623 B2 | 12/2018 | Leftly | |
| D837,394 S | 1/2019 | Cryan et al. | |
| D837,395 S | 1/2019 | Gan | |
| D841,178 S | 2/2019 | Lazarides et al. | |
| D841,825 S | 2/2019 | Rogers | |
| 10,245,208 B2 | 4/2019 | MacGuinness | |
| 10,314,762 B1 | 6/2019 | Marton et al. | |
| 10,406,024 B2 | 9/2019 | Evans et al. | |
| D863,573 S | 10/2019 | Ito et al. | |
| D865,986 S | 11/2019 | Cryan et al. | |
| 10,493,264 B1 | 12/2019 | Lefkovitz | |
| 10,555,681 B2 | 2/2020 | Sun | |
| 10,632,040 B2 | 4/2020 | Muench et al. | |
| D886,302 S | 6/2020 | Raghavan et al. | |
| D890,933 S | 7/2020 | Shurtliff et al. | |
| D891,626 S | 7/2020 | Xu | |
| 10,779,764 B2 | 9/2020 | Marlinski | |
| D905,253 S | 12/2020 | Hubelbank | |
| D910,858 S | 2/2021 | Marton et al. | |
| D917,054 S | 4/2021 | Woo | |
| D923,184 S | 6/2021 | Li | |
| D928,974 S | 8/2021 | Zulkosky et al. | |
| D932,035 S | 9/2021 | McDonough et al. | |
| D932,042 S | 9/2021 | Hu | |
| D932,638 S | 10/2021 | McDonough et al. | |
| D932,639 S | 10/2021 | McDonough et al. | |
| D932,640 S | 10/2021 | McDonough et al. | |
| D937,426 S | 11/2021 | Cordle | |
| D950,740 S | 5/2022 | Caneppele et al. | |
| D953,550 S | 5/2022 | Li | |
| D957,651 S | 7/2022 | Williams et al. | |
| D957,654 S | 7/2022 | Savchuk | |
| D961,889 S | 8/2022 | Chen | |
| 11,940,163 B1 | 3/2024 | Nazarian et al. | |
| 2001/0007952 A1 * | 7/2001 | Shimizu | A61F 7/02 |
| | | | 607/109 |
| 2005/0075593 A1 | 4/2005 | Smith et al. | |
| 2005/0193742 A1 | 9/2005 | Arnold | |
| 2007/0255187 A1 | 11/2007 | Branch | |
| 2008/0188915 A1 | 8/2008 | Mills et al. | |
| 2010/0249637 A1 | 9/2010 | Walter et al. | |
| 2010/0274162 A1 * | 10/2010 | Evans | A61H 15/0092 |
| | | | 601/46 |
| 2011/0000516 A1 | 1/2011 | Hershberger et al. | |
| 2011/0233185 A1 | 9/2011 | Augustine et al. | |
| 2012/0023785 A1 | 2/2012 | Barnes et al. | |
| 2013/0085552 A1 | 4/2013 | Mandel | |
| 2013/0238043 A1 * | 9/2013 | Beardall | A61F 7/007 |
| | | | 607/3 |
| 2014/0316311 A1 | 10/2014 | Nauman et al. | |
| 2014/0350441 A1 | 11/2014 | Shafieloo | |
| 2014/0364778 A1 | 12/2014 | Leftly et al. | |
| 2015/0121900 A1 * | 5/2015 | Yamazaki | A45D 44/00 |
| | | | 62/3.3 |
| 2015/0174002 A1 | 6/2015 | Burbank et al. | |
| 2015/0223975 A1 | 8/2015 | Anderson et al. | |
| 2016/0058657 A1 | 3/2016 | Lal et al. | |
| 2016/0089299 A1 | 3/2016 | Munoz | |
| 2016/0228325 A1 | 8/2016 | Kologrivov et al. | |
| 2016/0242956 A1 * | 8/2016 | Pilby Gomez | A61F 7/12 |
| 2016/0331631 A1 | 11/2016 | Odi | |
| 2016/0346153 A1 | 12/2016 | Hodges, IV | |
| 2016/0367425 A1 | 12/2016 | Wersland | |
| 2017/0042754 A1 | 2/2017 | Fowers et al. | |
| 2017/0113039 A1 | 4/2017 | Tuan | |
| 2017/0119620 A1 | 5/2017 | Trapp | |
| 2017/0290736 A1 | 10/2017 | Idris | |

(56) References Cited

U.S. PATENT DOCUMENTS

| | | |
|---|---|---|
| 2017/0304145 A1 | 10/2017 | Pepe |
| 2018/0042810 A1 | 2/2018 | Nguyen |
| 2018/0065517 A1 | 3/2018 | Kuhley et al. |
| 2018/0140506 A1 | 5/2018 | Smith et al. |
| 2018/0141188 A1 | 5/2018 | Lai |
| 2018/0147086 A1 | 5/2018 | Evans et al. |
| 2018/0228689 A1 | 8/2018 | Lach et al. |
| 2018/0303704 A1 | 10/2018 | Idris |
| 2019/0070068 A1 | 3/2019 | Pisharodi et al. |
| 2019/0151190 A1 | 5/2019 | Burbank et al. |
| 2019/0162460 A1* | 5/2019 | Oh .................. F25B 21/02 |
| 2019/0167330 A1 | 6/2019 | Kim |
| 2019/0183724 A1 | 6/2019 | Sifferlin |
| 2019/0290531 A1* | 9/2019 | Bosma .................. A61H 7/00 |
| 2019/0350752 A1* | 11/2019 | Aguiar .................. A61F 7/02 |
| 2020/0061316 A1 | 2/2020 | Inoue et al. |
| 2020/0068964 A1 | 3/2020 | Brandt et al. |
| 2020/0078261 A1 | 3/2020 | Duvall |
| 2020/0113773 A1 | 4/2020 | Ramanan et al. |
| 2020/0214927 A1 | 7/2020 | Clowney et al. |
| 2020/0224964 A1* | 7/2020 | Alexander .......... F25D 31/006 |
| 2020/0230021 A1 | 7/2020 | Pisharodi et al. |
| 2020/0253813 A1 | 8/2020 | Kuhns |
| 2020/0368061 A1 | 11/2020 | Levinson et al. |
| 2021/0330539 A1 | 10/2021 | Faussett |
| 2022/0192868 A1* | 6/2022 | Wersland .................. A61F 7/02 |
| 2023/0017326 A1* | 1/2023 | Alexander ............. F25B 21/02 |
| 2023/0372730 A1* | 11/2023 | Yu .......................... A61N 1/328 |
| 2023/0400233 A1* | 12/2023 | Jakobsen ............. F25D 31/007 |
| 2024/0125523 A1* | 4/2024 | Zhou .................. A61N 5/0616 |
| 2024/0230170 A1* | 7/2024 | Che ........................ F25B 21/02 |
| 2024/0350834 A1* | 10/2024 | Kang ................ A61N 1/36021 |

FOREIGN PATENT DOCUMENTS

| | | | | |
|---|---|---|---|---|
| CN | 205561041 U | * | 9/2016 | ............... F24F 1/02 |
| CN | 107530185 A | | 1/2018 | |
| CN | 209154892 U | | 7/2019 | |
| CN | 212996967 U | | 4/2021 | |
| CN | 114216172 A | * | 3/2022 | |
| KR | 101050069 B1 | | 7/2011 | |
| WO | 2015145471 A1 | | 10/2015 | |
| WO | WO-2017045909 A1 | * | 3/2017 | ............. F24F 1/022 |

* cited by examiner

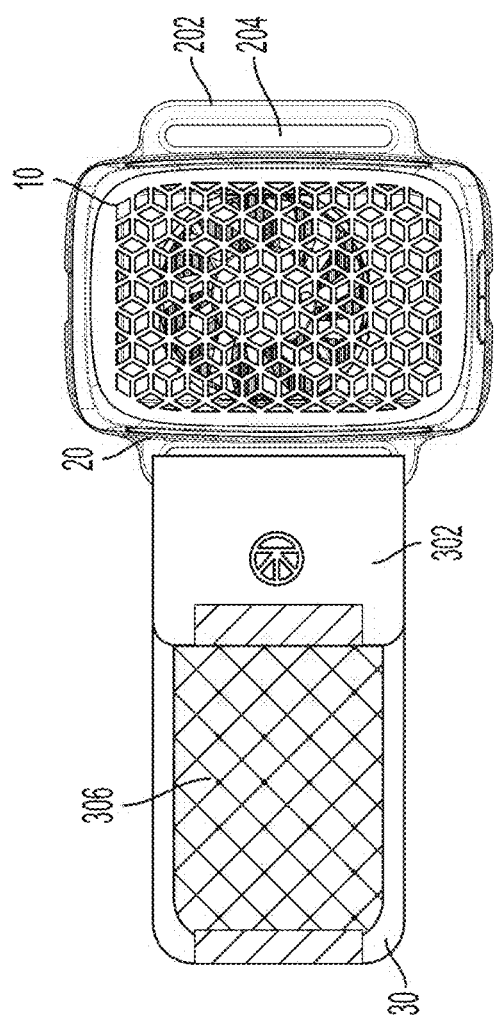
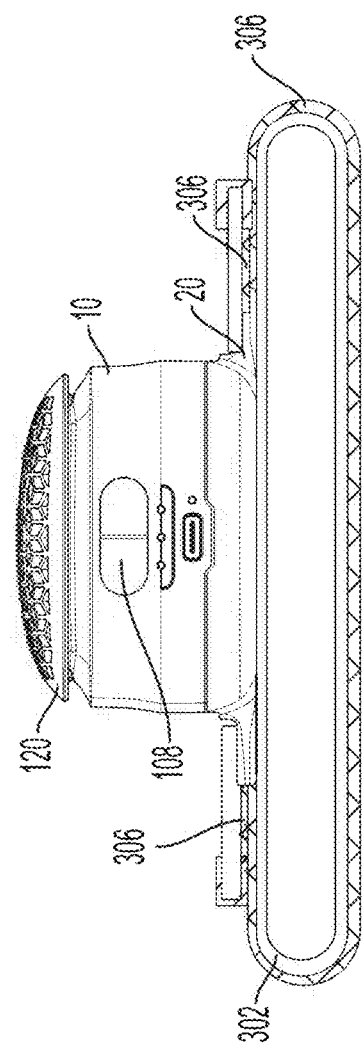
FIG. 21A
FIG. 21B

PORTABLE TEMPERATURE CONTROLLED DEVICE

CROSS-REFERENCE TO RELATED APPLICATIONS

This application is a continuation of PCT Application No. PCT/CN2024/108734, filed Jul. 31, 2024, which claims the benefit of U.S. patent application Ser. No. 18/362,349, filed Jul. 31, 2023 (now U.S. Pat. No. 11,940,163), and U.S. patent application Ser. No. 18/425,382, filed Jan. 29, 2024, the contents of which are incorporated herein in their entirety.

TECHNICAL FIELD

The present disclosure relates to a temperature-controlled device, more specifically, a hand-held portable temperature-controlled device.

BACKGROUND

Cooling and heating devices are used for therapeutic purposes or during surgical procedures due to many known benefits of hot and/or cold therapy in treatment. Accordingly, various apparatuses have been devised to achieve the desired heat and/or cold transfer. One issue with current heating and/or cooling devices is lack of portability and maneuverability. Bulky devices are often used to heat and cool the affected areas to provide fast and efficient heat transfer. The size of these devices is typically necessary because components are not optimally arranged or configured to promote efficient operation. These heating and cooling devices are often heavy, need to be in a fixed position, and plugged into a continuous power supply. Smaller and lighter multi-therapy devices are desirable. One potential hurdle to a smaller form factor has been managing heat dissipation within a portable device to protect the internal components from overheating. Accordingly, a need exists for a light portable device that provides heating and cooling therapy comparable to the bulky device while also providing efficient heat management. It is further desirable to provide a versatile multi-therapy device that can be used on different body parts of a user, whether manually by the user or, if desired, in a fixed position.

The background description disclosed anywhere in this patent application includes information that may be useful in understanding the present disclosure. It is not an admission that any of the information provided herein is prior art or relevant to the presently claimed concepts, or that any publication specifically or implicitly referenced is prior art.

SUMMARY

Described herein is a novel portable temperature-controlled device for therapeutic applications including both cold and heat therapies within a compact and handheld device. In some aspects, the portable temperature-controlled device is assembled with an adjustable strap system to wrap around a patient body part. The temperature-controlled device is designed to have an ergonomic configuration to be comfortably held by one hand, while placing the device on a desired area of the body. These areas can include the back, knee, elbow, shoulder, ankle, face, neck, etc. The temperature-controlled device can be further assembled with a strap to secure on the body part to free the user's hand.

The temperature-controlled device can include a thermoelectric element to transfer heating and cooling to the user's body. In a typical implementation, the thermoelectric element is a device that utilizes the Peltier Effect, having one side of which cools while the other side heats. The heating and cooling modes can be optionally and selectively switched within predetermined temperature ranges. The temperature-controlled device can further include a rechargeable battery for prolonged use.

In one aspect, a hand-held portable temperature-controlled device includes a housing having a generally cuboid shape with curved surfaces and configured to be grasped by one hand. The housing may include: a controllable temperature element having a first surface and a second surface and configured to generate cooling and heating; a heat sink disposed on the first surface of the controllable temperature element; a fan disposed on the heat sink and configured to direct heat away from the heat sink; a heat spreader comprising a first side and a second side, the first side extending out from the housing and contacting a user's body part; a support member configured to support the heat sink and the fan; and a temperature controller connected to the controllable temperature element. The housing further includes a first air inlet configured to permit air flow into the housing and an air outlet configured to permit air flow to flow out of the housing, and the first air inlet and the air outlet are in fluid communication with each other.

In another aspect, a wearable assembly includes a temperature-controlled device which comprises a housing having a generally cuboid shape. The housing may include: a controllable temperature element having a first surface and a second surface; a heat sink disposed on the first surface of the controllable temperature element; a fan disposed on the heat sink and configured to direct heat away from the heat sink; a heat spreader comprising one side and another side and configured to receive thermal energy from the controllable temperature element; and a support member configured to support at least one battery, the heat sink, and the fan. The wearable assembly includes a strap case configured to be assembled to the temperature-controlled device. The strap case may comprise: a center opening through which the heat spreader extends on a bottom side; and a pair of side arms curvedly, integrally extending upward, each having a protrusion protruding toward the center opening.

In yet another aspect, a hand-held portable temperature-controlled device includes a cylindrical housing comprising an air inlet and an air outlet in fluid communication with each other, wherein the air inlet is configured to permit air to flow into the cylindrical housing and the air outlet is configured to permit the air to flow out of the cylindrical housing. A fan can be located within the cylindrical housing, and a heat sink can be disposed adjacent to the fan. A first portion of the heat sink can be located within the cylindrical housing and a second portion of the heat sink can be located outside of the cylindrical housing. The hand-held portable temperature-controlled device can also include a controllable temperature element comprising a first surface located opposite a second surface and can be configured to generate heating and cooling. The second surface of the controllable temperature element can be disposed adjacent to the second portion of the heat sink. The hand-held portable temperature-controlled device can also include a heat spreader comprising a bottom surface located opposite a top surface, wherein the bottom surface can be disposed adjacent to the first surface of the controllable temperature element and the top surface can be configured to contact a face of a user. The top surface can be oriented at a non-zero angle relative to the bottom surface.

Further features and advantages, as well as the structure and operation of various aspects, are described in detail below with reference to the accompanying drawings. It is noted that the specific aspects described herein are not intended to be limiting. Such aspects are presented herein for illustrative purposes only. Additional aspects will be apparent to persons skilled in the relevant art(s) based on the teachings contained herein.

BRIEF DESCRIPTION OF THE DRAWINGS

The accompanying drawings, which are incorporated herein and form a part of the specification, illustrate aspects of the present disclosure and, together with the description, further serve to explain the principles of the disclosure and to enable a person skilled in the pertinent art to make and use the disclosure.

FIGS. 21A and 21B are top and side views of the portable therapeutic temperature-controlled device assembled with the primary strap.

In the drawings, like reference numbers generally indicate identical or similar elements. Additionally, generally, the left-most digit(s) of a reference number identifies the drawing in which the reference number first appears.

DETAILED DESCRIPTION

Figure 1:
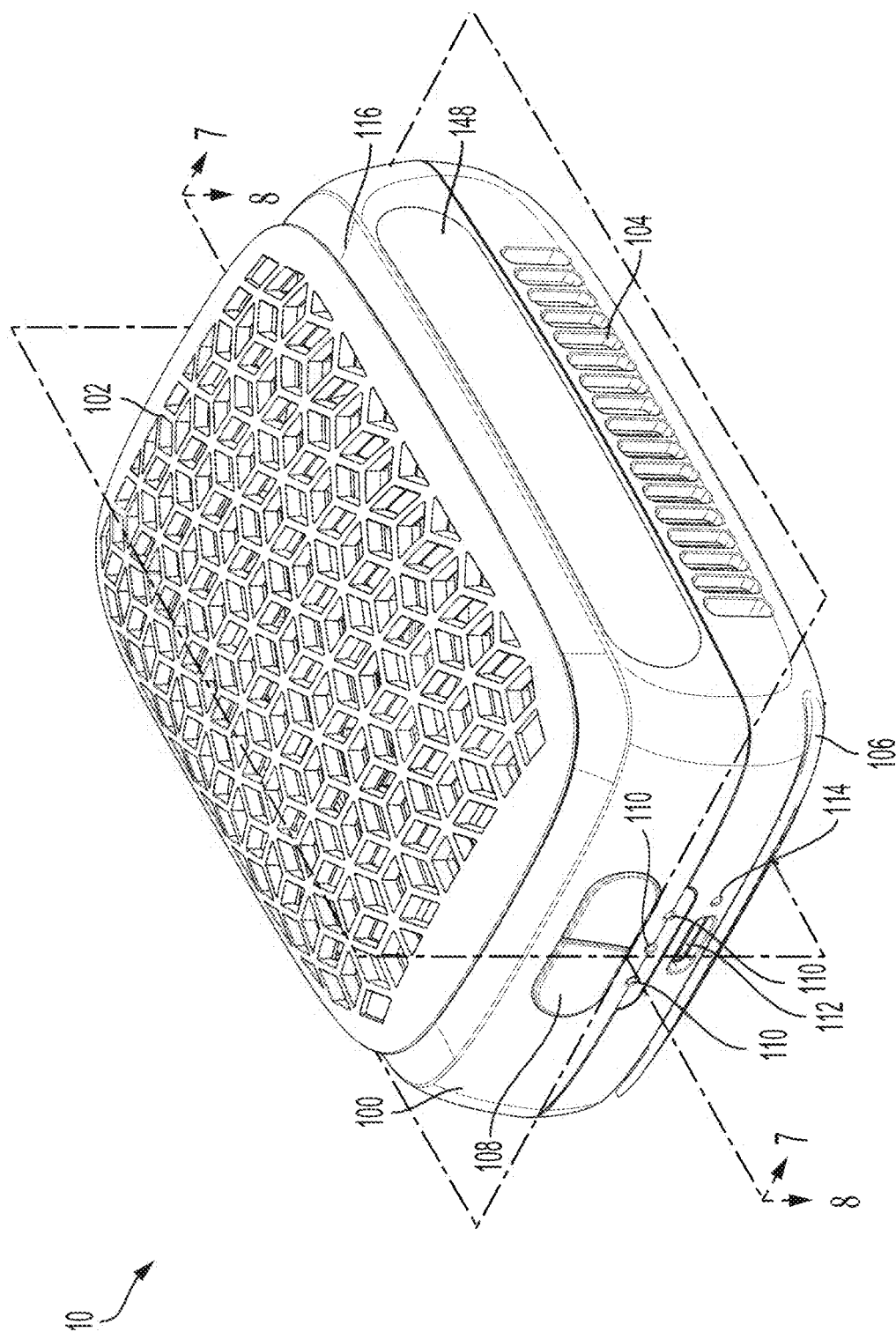
FIG. 1 is a perspective view of a portable therapeutic temperature-controlled device according to aspects of the present disclosure.

The following description and drawings are illustrative and are not to be construed as limiting. Numerous specific details are described to provide a thorough understanding of the disclosure. However, in certain instances, well-known or conventional details are not described in order to avoid obscuring the description. References to one or more aspects in the present disclosure can be, but not necessarily are references to the same aspect; and, such references mean at least one of the aspects. If a component is not shown in a drawing then this provides support for a negative limitation in the claims stating that that component is "not" present. However, the above statement is not limiting and in another aspect, the missing component can be included in a claimed aspect.

Reference in this specification to "one aspect," "an aspect," "a preferred aspect" or any other phrase mentioning the word "aspect" means that a particular feature, structure, or characteristic described in connection with the aspect is included in at least one aspect of the—disclosure and also means that any particular feature, structure, or characteristic described in connection with one aspect can be included in any aspect or can be omitted or excluded from any aspect. The appearances of the phrase "in one aspect" in various places in the specification are not necessarily all referring to the same aspect, nor are separate or alternative aspects mutually exclusive of other aspects. Moreover, various features are described which may be exhibited by some aspects and not by others and may be omitted from any aspect. Furthermore, any particular feature, structure, or characteristic described herein may be optional. Similarly, various requirements are described which may be requirements for some aspects but not other aspects. Where appropriate any of the features discussed herein in relation to one aspect or aspect of the disclosure may be applied to another aspect or aspect of the disclosure. Similarly, where appropriate any of the features discussed herein in relation to one aspect or aspect of the disclosure may be optional with respect to and/or omitted from that aspect or aspect of the disclosure or any other aspect or aspect of the disclosure discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various aspects given in this specification.

Without intent to further limit the scope of the disclosure, examples of instruments, apparatus, methods and their related results according to the aspects of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present disclosure.

The terms "connected" or "coupled" and related terms are used in an operational sense and are not necessarily limited to a direct connection or coupling. The term "thermally coupled" means coupled in a way capable of conducting heat, and the term "thermally insulated" means separated by a substance that deters heat transfer.

The term "flexible" generally means bendable and adaptable under relatively little force. In the context of various aspects of the present disclosure, flexible is intended to describe the dynamic conforming nature of the personal temperature controlled device to the general shape of a portion of a person's body, such as wrist, ankle, neck, shoulder, back, chest, forehead, rib cage, arch, temple, palm, etc., directly or indirectly in contact with or otherwise engaging a surface of the personal temperature-controlled device. In addition, the term "approximately" is generally used to modify a numerical value above and below the set value by a variation of +/−10%.

Figure 9:
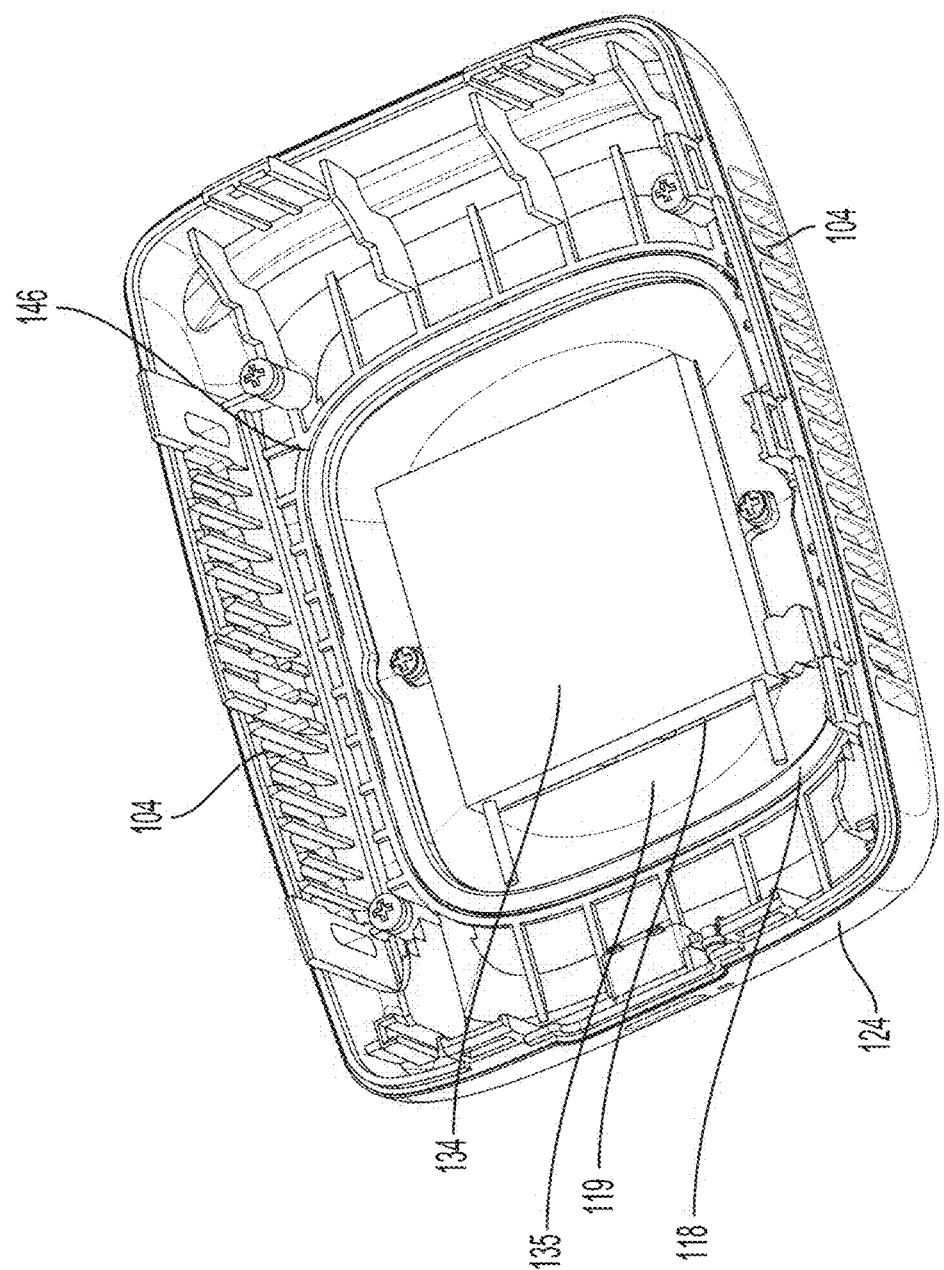
FIG. 9 is an interior of a lower housing of the portable therapeutic temperature-controlled device according to aspects of the present disclosure.
Figure 10:
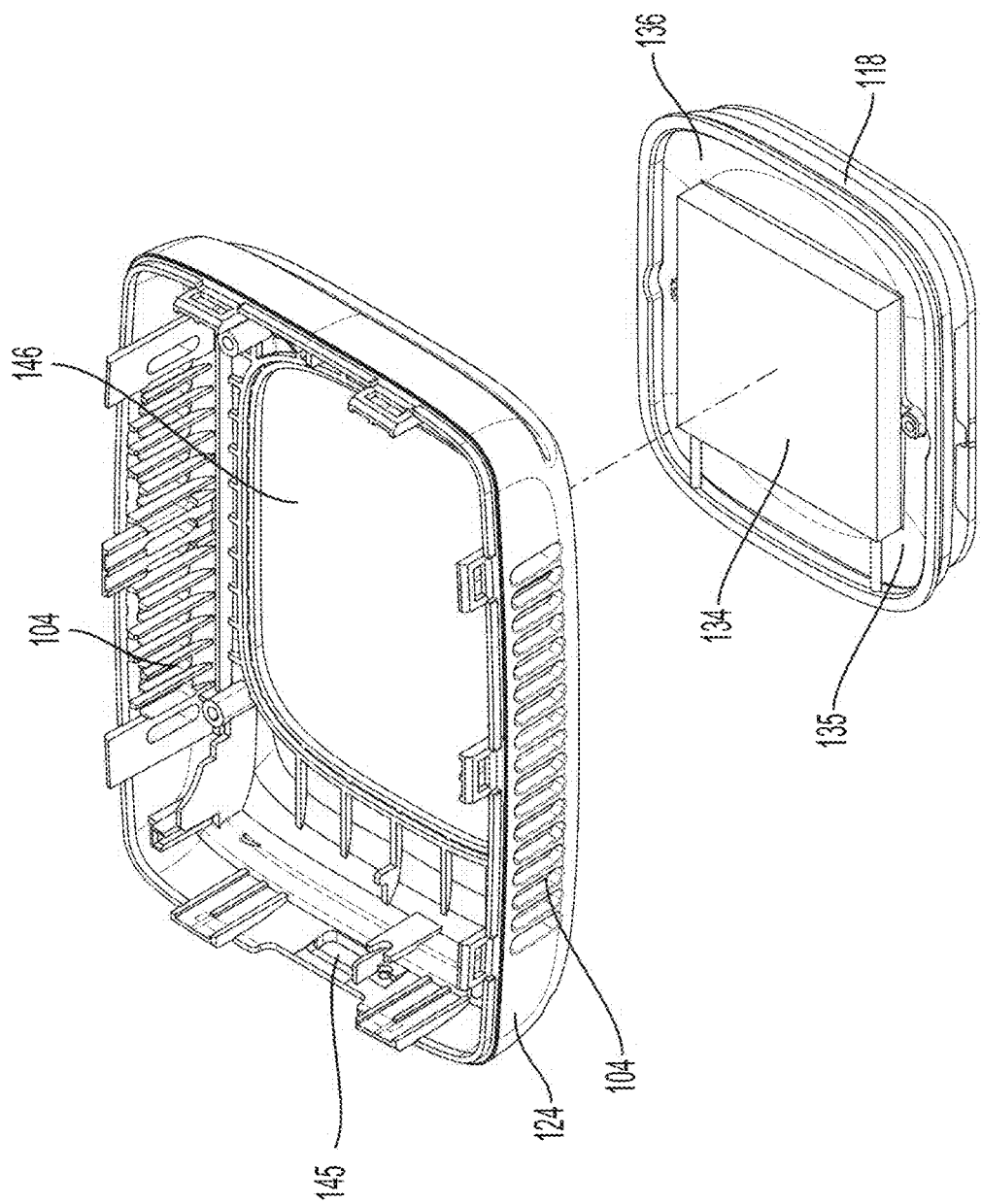
FIG. 10 is an exploded view of FIG. 9.
Figure 11:
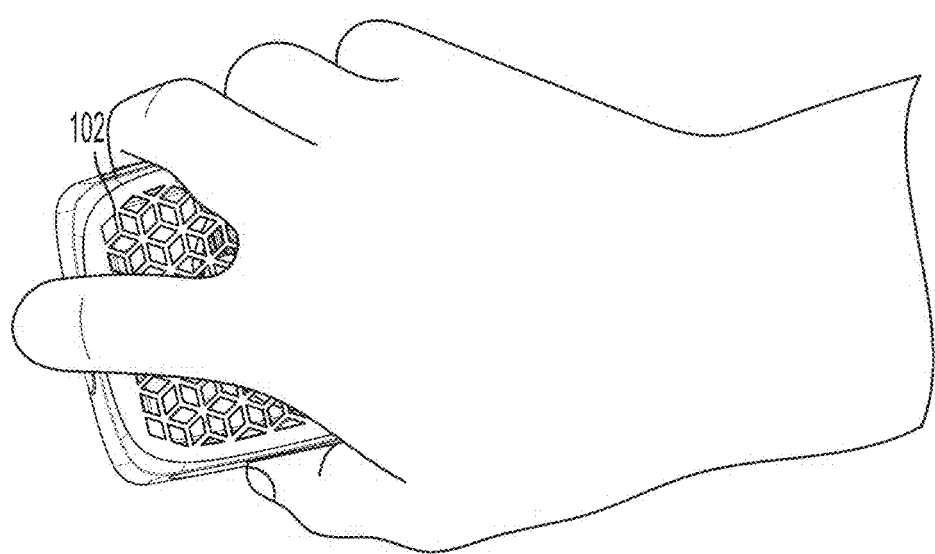
FIG. 11 is a top view of the portable therapeutic temperature-controlled device grasped by a user's hand.
Figure 12:
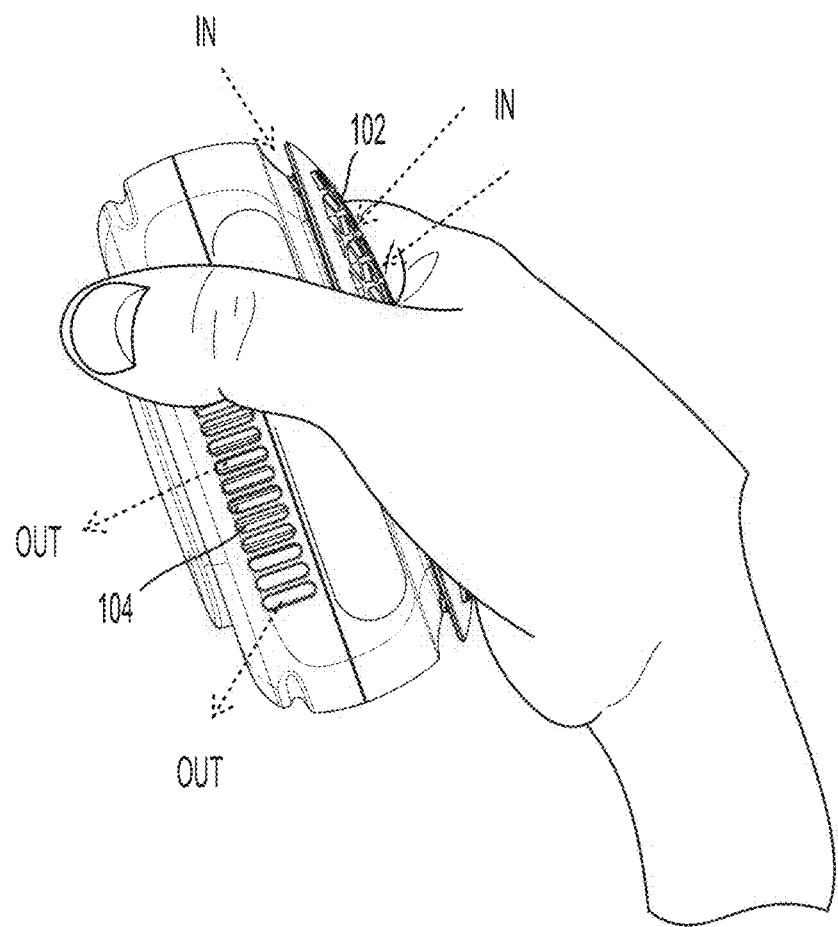
FIG. 12 is a side view of the portable therapeutic temperature-controlled device grasped by a user's hand.

Described herein and shown in FIGS. 1-10 is an exemplary temperature-controlled device that can provide cooling and heating effects. FIGS. 11 and 12 show the temperature-controlled device grasped by a user's hand.

FIG. 1 shows a temperature-controlled device 10 designed for a user to comfortably grasp by one hand while providing a heating or cooling therapeutic effect to a desired area on the user's body and also promoting air flow into and out of the temperature-controlled device 10. In some aspects, the temperature-controlled device 10 includes a housing 100, on an outer side of which includes an air inlet or a first air inlet 102 on a top surface of the temperature-controlled device 10, an air outlet 104 on at least one side surface (e.g., at least one of a first side surface or a second side surface of the temperature-controlled device 10, a pair of recesses 106 on opposing side surfaces, a plurality of buttons 108 for selectively controlling a heating mode and a cooling mode of a temperature mode by user manipulation, a first or control mode Light-Emitting Diode (LED) 110 disposed below the buttons 108 for indicating the temperature mode, a Universal Serial Bus (USB) charging port or simply charging port 112, a second or battery level LED 114, and an undercut 116. In some aspects, the first LED 110 may include one or more LEDs. In some aspects, the overall shape of the housing 100 may be curvedly shaped and dimensioned for ergonomic holding by a user's hand. In further aspects, each element of the temperature-controlled device 10 is arranged and designed to provide efficient operation of the heating and cooling effect and optimal heat dissipation in a compact space, as will be described later. For example, the housing 100 may be rectangular in shape to allow for one-handed holding while maximizing the size of air inlet 102.

Figure 2:
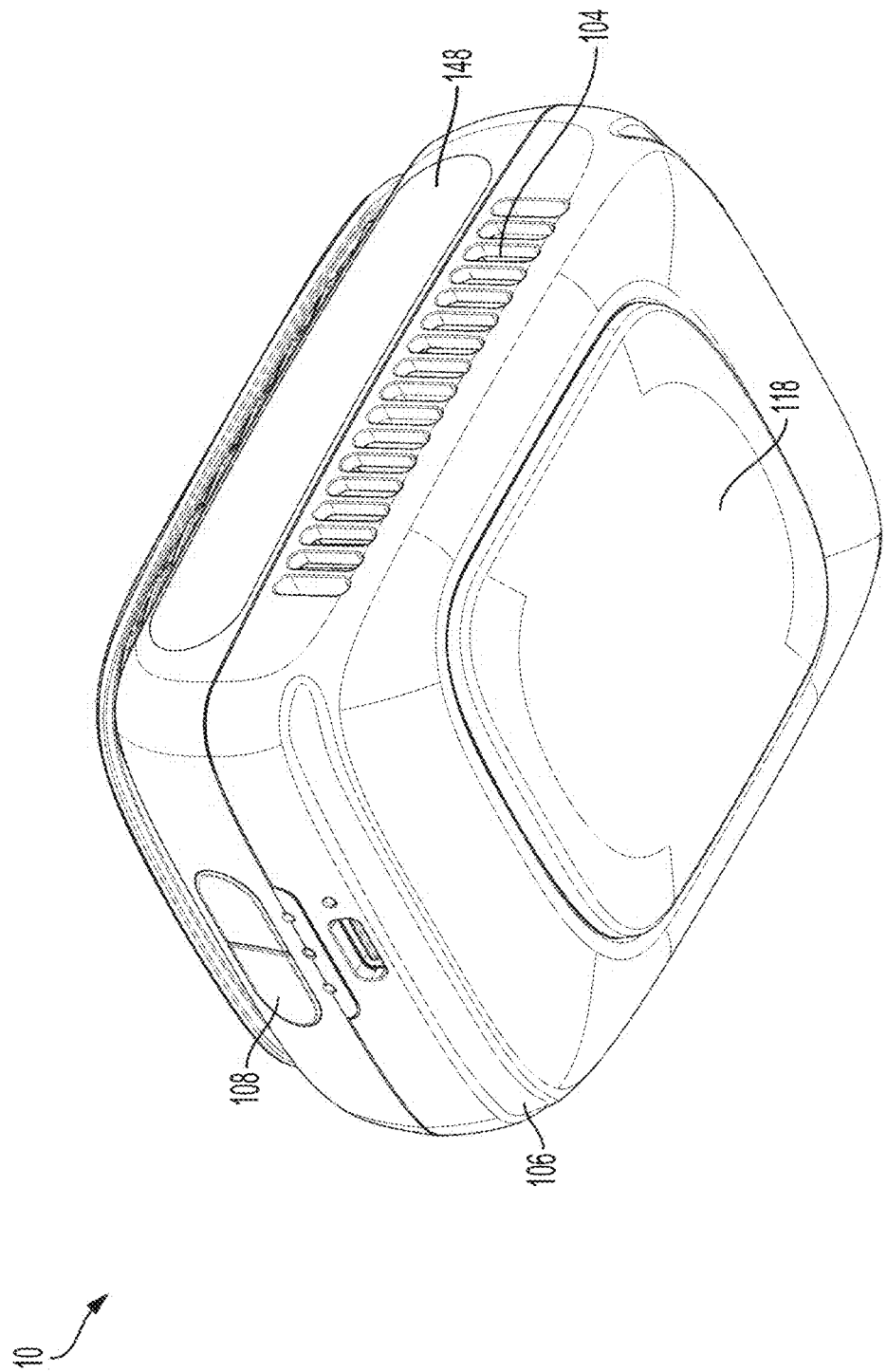
FIG. 2 is another perspective view of the portable therapeutic temperature-controlled device according to aspects of the present disclosure.
Figure 3:
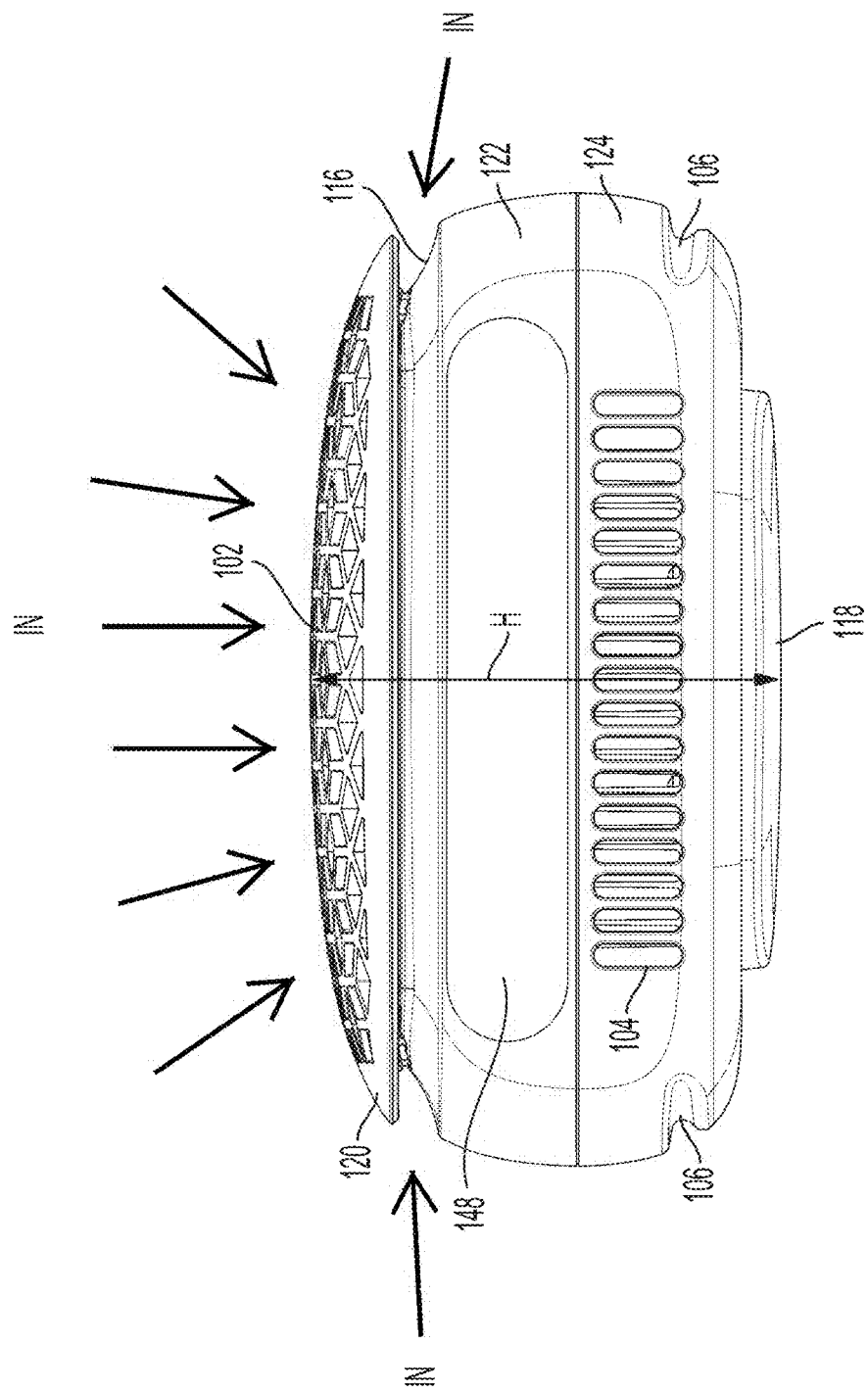
FIG. 3 is a side view of the portable therapeutic temperature-controlled device according to aspects of the present disclosure.

Referring to FIGS. 2 and 3, in some aspects, the temperature-controlled device 10 further includes a heat spreader 118 on the bottom side of the housing 100. In some aspects, the heat spreader 118 may be implemented as a metallic heat spreader and can be made of high thermal conductive materials, such as, for example, copper, aluminum, or other metals or metal alloys, or certain ceramics, to help transfer heat or cold to increase the effective area of heating or cooling treatment. As will be described later, the housing 100 has an opening (e.g., "146" in FIGS. 6 and 10) defined in the bottom side of the housing 100 through which the heat spreader 118 extends out of the housing 100. While the housing 100 may be formed of, e.g., a plastic material, the bottom portion of the housing 100 exposes the heat spreader 118, which in some aspects may be constructed of a metal material. Thus, the heat spreader 118 may have one side exposed outside that can directly transfer thermal energy to a body part of the user. In addition, this configuration allows engagement with a strap case, which will be described later, while ensuring that the exposed side of the heat spreader 118 maintains direct contact with the user's skin.

Figure 4:
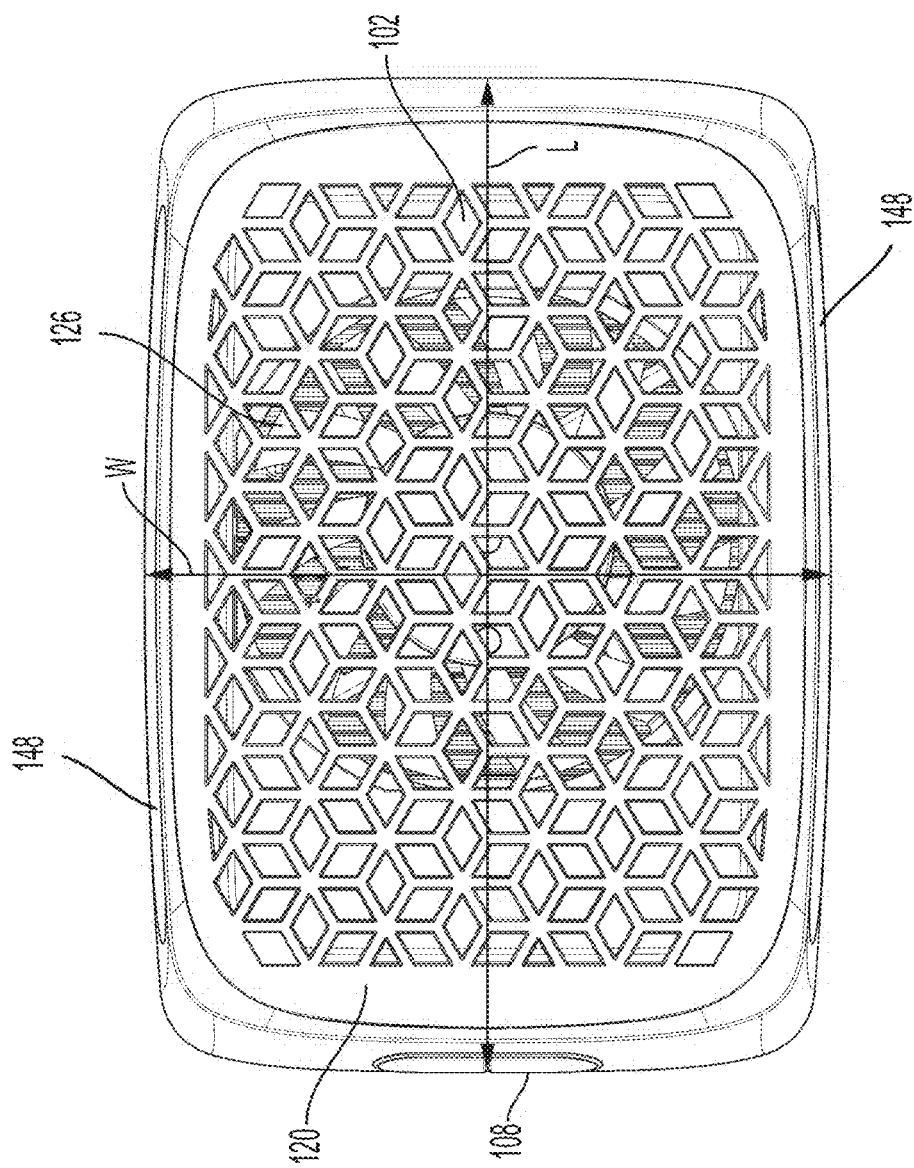
FIG. 4 is a top view of the portable therapeutic temperature-controlled device according to aspects of the present disclosure.

Referring to FIGS. 3 and 4, in some aspects, the temperature-controlled device 10 has a generally cuboid shape with curved surfaces and may have a dimension that a user can easily grasp by one hand. For example, the housing 100 may have a length approximately between 110 mm and 115 mm (L), a width approximately between 75 mm and 80 mm (W), and a height approximately between 52 mm and 58 mm (H). This is one exemplary dimension such that each of length, width, and height may be smaller or greater than what's described herein. The housing 100 may be formed of a plastic material, e.g., one or more bonded layers of one or more of polyester (polyether), polyethylene, polypropylene, nylon, kevlar, nomex, polyacrylonitrile, cellulose, polyurethane, polycarbonate, and acrylonitrile-butadiene-styrene terpolymer, or similar foams and/or fibers. However, it is not limited to the listed materials for the housing 100, but any non-metallic materials, metallic, wood, or the like could be properly implemented. In addition, the housing 100 is curvedly shaped so as to be ergonomic and to facilitate gripping by a user's hand.

To promote proper one-handed gripping, the upper portion of the outer side surfaces has grip portions 148 inwardly curved forming a concave surface to provide comfort grasp particularly for fingers. Such a shape can induce a user to hold the temperature-controlled device 10 in a certain position as shown in FIGS. 11 and 12. The shape and dimensions of housing 100 are configured so as to prevent the buttons 108, the first LEDs 110, the charging port 112, and the second LED 114 from being accidentally gripped or covered when the user is holding the temperature-controlled device 10. Further, the size and dimensions of the air inlet 102 and the air outlet 104 are configured such that they are exposed, partially or entirely, when a user is gripping the temperature-controlled device 10, which facilitates air flow within the housing 100 even when the temperature-controlled device 10 is being held. However, the shape is not limited to what is shown in the drawings or described above. In other words, the temperature-controlled device 10 may have a cylindrical shape, a spherical shape, a hemispheric shape, a prism shape (e.g., triangular prism, hexagonal prism, pentagonal prism, or the like), a cone shape, a tetrahedron shape, an octahedron shape, etc.

The configurations according to various aspects enable the compact size and light weight of the temperature-controlled device 10, as well as efficient and portable power management, which enables a user to engage in an active life-style while still obtaining a thermal therapy. Further, overheating of the temperature-controlled device 10 can be prevented.

Referring back to FIG. 3, the housing 100 may include individually configured parts assembled together, including a top cover 120 having a convex shape, an upper side cover 122, and a lower side cover 124. The top cover 120 forms a top portion of the housing 100, the upper side cover 122 is assembled to the top cover 120, and the lower side cover 124 is then assembled to the upper side cover 122. Each cover may be configured with a curved surface such that the top cover 120, the upper side cover 122, and the lower side cover 124 together form a convex contour of the housing 100 for ergonomic design. In addition, the upper side cover 122 and the lower side cover 124 are assembled forming a partially enclosed space of the housing 100 together with the top cover 120.

The top cover 120 may include a first plurality of vents or openings that form the air inlet 102 to be formed on an upper surface or top surface of the housing 100. The first plurality of vents may be defined on the entire surface, or partially, of the top cover 120. The air inlet 102 may be configured to guide air flow into the housing 100 through the first plurality of vents. For instance, a fan ("126" in FIG. 4) may be located adjacently under the top cover 120 to cause the air flow to flow into the housing 100 through the first plurality of vents. The lower side cover 124 may be formed with a second plurality of vents or openings on the longer (longitudinal) side of the lower side cover 124 of the housing 100 as the air outlet 104 to permit the air flow to flow or exit out from the housing 100, on the shorter (width) side of the lower side cover 124, or a combination of both. Accordingly, the first plurality of vents and the second plurality of vents are configured to define an air flow passage for the air flow in and out of the housing 100. In addition, an air flow passage may be formed from the first plurality of vents as the air inlet 102 and the undercut 116 as a third opening to the second plurality of openings as the air outlet 104 through the fan 126 and the heat sink 132.

Alternatively or additionally, the second plurality of vents or openings may be formed on one side surface, two side surfaces (e.g., opposite side surfaces), three side surfaces, or all four side surfaces of the lower side cover 124. For instance, FIG. 3 shows the air outlet 104 as the second plurality of vents or openings formed on a first surface, while FIGS. 9 and 10 show the air outlet 104 formed on the first surface and a second surface which faces the first surface. In some aspects, the second plurality of vents are arranged longitudinally along the corresponding surface. The plurality of vents or openings of the lower side cover 124 may form the air outlet 104, which may be configured to facilitate the air flow out of the housing 100. In some aspects, the air outlet 104 may be provided on opposite longer (longitudinal) sides or surfaces of the lower side cover 124 (e.g., the first and second side surfaces facing each other) to guide inside air to flow out of the housing 100 in opposing directions. In some aspects, the air outlet 104 is formed on side surfaces of the housing 100 so as to avoid air flowing out from the air outlet 104 does not blow onto a user's skin. In some aspects, the air outlet 104 is positioned on the side surface the housing 100 so as to prevent the user from being able to obstruct air flow while holding the housing 100.

The housing 100 may further include a fan 126 configured to draw or pull outside air into the housing 100. Referring to FIG. 4 which shows a top view of the temperature-controlled device 10, the fan 126 may be located directly, adjacently below the top cover 120 for drawing outside air into the housing 100 through the air inlet 102. The fan 126 is configured to circulate the air inside the housing 100 and guide out, through the air outlet 104, to exit the housing 100.

Referring back to FIG. 3, the pair of recesses 106 that are surface-treated may be formed on opposing side surfaces (e.g., third and fourth surfaces positioned facing each other in a width direction) of the lower side cover 124. In some aspects, the recesses 106 are formed on the sides where the air outlet 104 are not defined. For example, the air outlet 104 may be formed on the longer (longitudinal) side or sides of the lower side cover 124 while the recesses 106 may be formed on the shorter (width) side or sides of the lower side cover 124 as illustrated in FIG. 3. In other aspects, the air outlet 104 and the recesses 106 may be configured on the same side of the lower side cover 124. The recesses 106 may be configured to receive a strap case which will be described below.

In some aspects, the upper side cover 122 may include an undercut 116 configured as a recessed surface positioned along an upper edge of the upper side cover 122 adjacent to the top cover 120. The undercut 116 can form a gap between the top cover 120 and the upper side cover 122 and is configured to facilitate additional and/or alternative air to flow into the housing 100. That is, in some aspects, the undercut 116 may be implemented with the air inlet 102 as a second air inlet such that air is permitted to flow into the housing 100 through the air inlet 102 and additional air through the undercut 116, as shown by the arrows in FIG. 3. In other aspects, the housing 100 may comprise only one of the air inlet 102 and the undercut 116 to receive air.

When a user is grasping the temperature-controlled device 10 by one hand, with reference to FIGS. 11 and 12, the air inlet 102 may be, partially or entirely, blocked and air flow into the housing 100 may be partially obstructed by the user's hand. In any situation, the undercut 116 is configured to provide an additional air passage for additional air to be drawn into the housing 100 to supplement the air flow of the air inlet 102. The air inlet 102, the undercut 116, and the fan 126 are configured to facilitate air flow through a central path within an internal cavity of the housing 100 of the temperature-controlled device 10. For instance, the air inlet 102 together with the undercut 116 and the air outlet 104 are in fluid communication with each other via the central path within the internal cavity (for example, see shaded area "A" in FIG. 7). Maximal air flow in housing 100 can be provided by the combination of the air inlet 102, the undercut 116, and the fan 126, along with the physical arrangement of components within housing 100 within the temperature-controlled device 10. The increased air flow that results from this arrangement allows the temperature-controlled device 10 to operate efficiently (e.g., fast cooling, fast heating) in the heating, cooling, and contrast modes in a portable handheld device.

Figure 5:
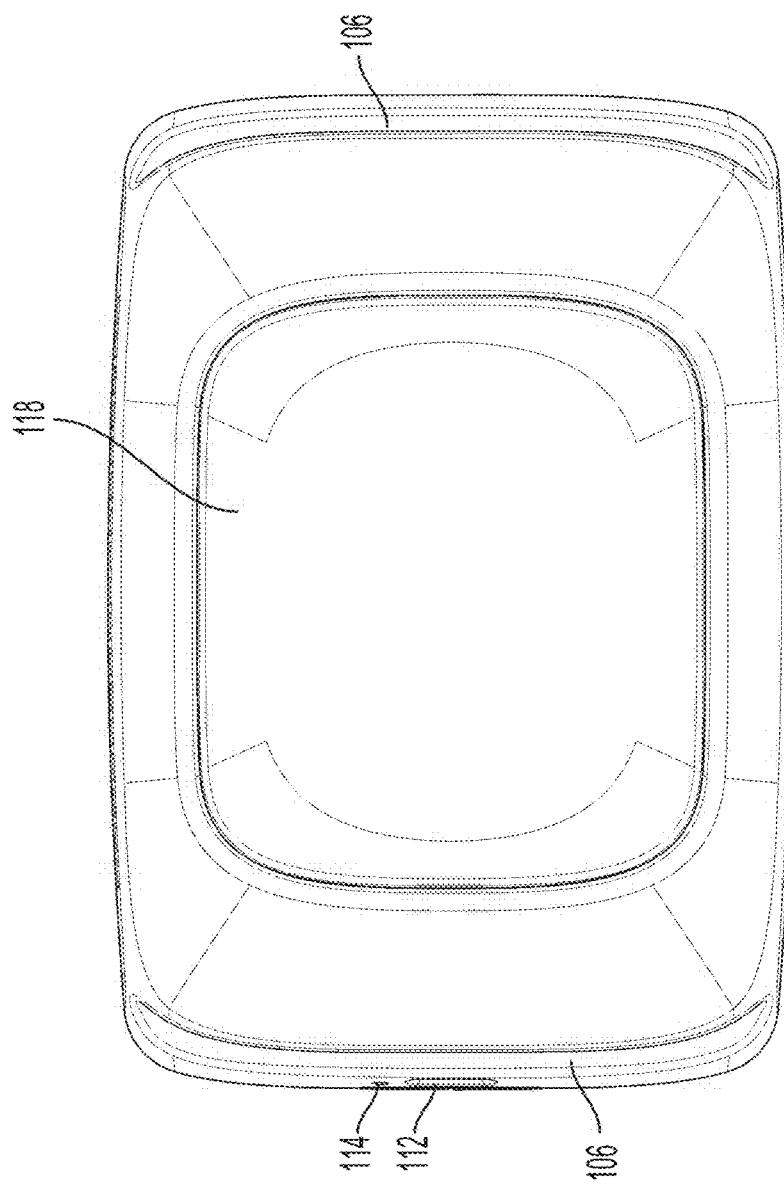
FIG. 5 is a bottom view of the portable therapeutic temperature-controlled device according to aspects of the present disclosure.

Referring to FIG. 5, the bottom portion of the housing 100 has an opening (e.g., "146" in FIGS. 6 and 10), which will be described later, through which the heat spreader 118 extends out of the housing 100. In some aspects, the heat spreader 118 is configured with dimensions to extend outside of the housing 100 and beyond a strap case 20 when it is attached to housing temperature-controlled device 10 (see FIG. 14). The heat spreader 118 may be dimensioned so that it is in contact with a skin surface of the user when the temperature-controlled device 10 is used with or without strap case 20. The heat spreader 118 may have a convex-shaped bottom surface to facilitate contact with surface of the user's body and align with the overall curved shape of the housing 100. With such a convex configuration, the amount of material used for the heat spreader 118 may be reduced while maintaining or improving the heat transfer performance. In addition, the heat spreader 118 may be configured to increase or decrease the temperature of about, e.g., Δ8° C. in about, e.g., 150 seconds, so as to quickly and efficiently deliver the desired temperature to a user. As will be further described later, the heat spreader 118 is designed for material/weight reduction to satisfy the compactness. In some aspects, the heat spreader 118 may be formed of a conductive alloy, metal, or material, such as aluminum, stainless steel, carbon-fiber, or carbon-carbon materials and/or composites. The dimensions of the spreader 118 may be tailored for the particular application. Such dimensions as well as the shape may be configured to reduce amount of material used while increasing the contact area with a user. For example, curved outer surfaces, rather than flat surfaces, can enhance the contact with the user's body, or unnecessary materials can be removed to reduce the overall size and weight.

Internal components of the temperature-controlled device 10 and their arrangement within housing 100 will be described in detail with reference to FIGS. 6-10.

Figure 6:
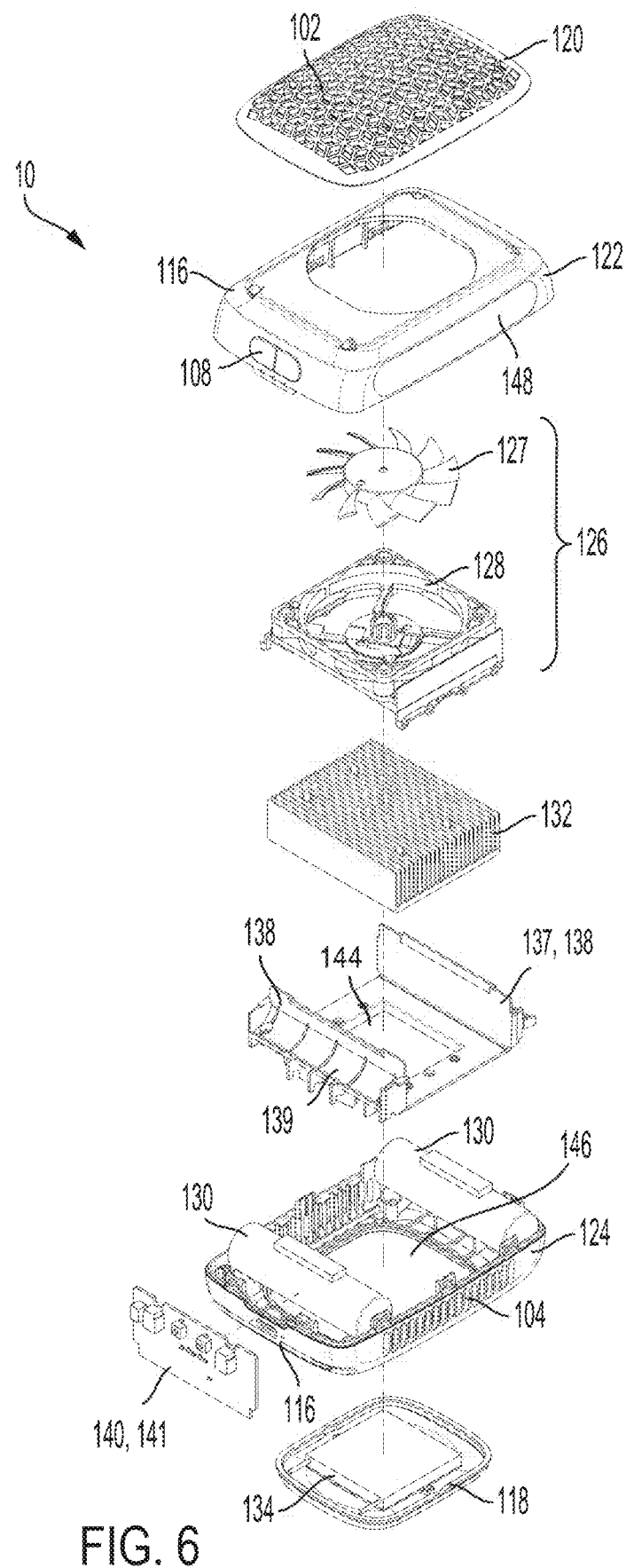
FIG. 6 is an exploded view of the portable therapeutic temperature-controlled device according to aspects of the present disclosure.

FIG. 6 is an exploded view of the temperature-controlled device 10, where each case part of the housing 100 is opened to show internal components of the temperature-controlled device 10 enclosed inside the housing 100. As described above, the temperature-controlled device 10 includes the fan 126 that may be composed of a fan blade portion 127 and a fan housing 128. The fan 126 may be arranged adjacently below the top cover 120 inside the housing 100 to pull ambient air into the housing 100 via the air inlet 102. In some aspects, a heat sink 132 may be arranged beneath the fan 126. The heat sink 132 may be disposed on a first surface of controllable temperature element 134, which can generate cooling and heating. In some aspects, the first surface of controllable temperature element 134 is an upper surface. Examples of the controllable temperature element 134 include a Peltier device, Peltier heat pump, solid state refrigerator, thermoelectric cooler (TEC), etc. The controllable temperature element 134 may adapt the Peltier effect to create a heat flux at the junction of two different types of materials, and transfer heat from one side of the device to the other. In some aspects, a second surface of the controllable temperature element 134 is in contact with a first side (or one side) of the heat spreader 118 so as to transfer thermal energy to the upper surface of the heat spreader 118. In some aspects, the second surface may oppose the first surface; for example, when the first surface is implemented as an upper surface of controllable temperature element 134, the second surface may be implemented as a lower surface of controllable temperature element 134. A second side (or another side) of the heat spreader 118 that opposes the first side of the heat spreader 118 may be disposed inside the housing 100. The first side of the heat spreader 118 may extend out from the housing 100.

The heat sink 132 can pull heat from the upper surface of the controllable temperature element 134, and the fan 126 can help dissipate heat or direct heat away from the heat sink 132 and other components. When the temperature-controlled device 10 is in use, the heat spreader 118 is cooled or heated by the controllable temperature element 134 and the heat or cold can be transferred to, by contacting, a user via the heat spreader 118. In some aspects, the temperature-controlled device 10 further includes a printed circuit board or PCB 140 for electrical and data communication. The PCB 140 may include a control unit (e.g., temperature controller) 142 connected to communicate with the controllable temperature element 134 for various control functions (e.g., turning on or off the temperature-controlled device 10, heating or cooling, etc.).

The controllable temperature element 134 may be implemented as a heat pump that can directly convert electricity into heating and cooling power depending on the mode of the temperature-controlled device 10. When power is supplied to the controllable temperature element 134, the current causes one side (cool side) of the controllable temperature element 134 to absorb heat. The opposite side of the controllable temperature element 134 may then release heat (the hot side). For instance, when a user presses one of buttons 108 for a heating mode, one side of the controllable temperature element 134 releases heat where the one side is in contact with the user. When a user presses one of buttons 108 for a cooling mode, on the other hand, the same side of the controllable temperature element 134 may absorb heat rather than releasing the heat to provide a cooling effect to the user. Further, during a contrast mode, the controllable temperature element 134 may be controlled to periodically alternate heat release and absorption functions. That is, the controllable temperature element 134 causes heat to flow from the cool side to the hot side. Reversing the current causes the heat to be moved in the opposite direction thereby reversing the hot side and the cold side. Consequently, the heating or cooling effect can be selectively performed. Based on the disclosure provided herein, one of ordinary skill in the art will recognize the various possible reconfigurations of temperature-controlled device 10 that would achieve a heating/cooling effect.

The controllable temperature element 134 may have dimensions of approximately, e.g., 40 mm (L)×40 mm (W)×4.8 mm (D), while the heat sink 132 has a surface area slightly greater than the controllable temperature element 134. The fan 126 may have the overall dimensions of approximately, e.g., 60 mm (L)×60 mm (W)×10 mm (D). The heat spreader 118 may have dimensions of approximately, e.g., 70 mm (L)×60 mm (W)×7 mm (D). The disclosed dimensions are however not limited to these numeric values and may be configured within a range of sizes to maintain the ability for one-handed gripping of the temperature-controlled device 10.

Figure 7:
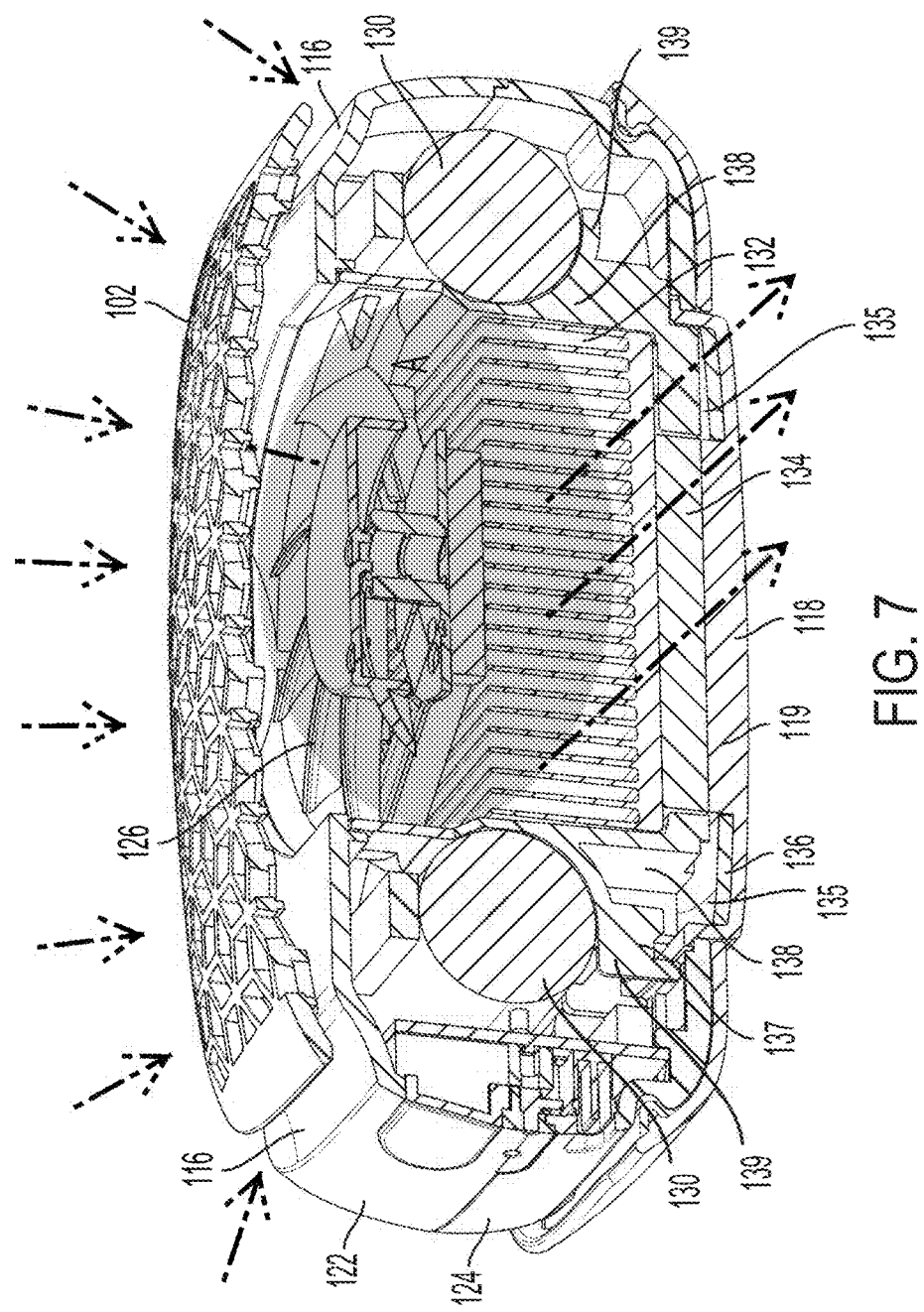
FIGS. 7 and 8 are cross-sectional views of the portable therapeutic temperature-controlled device according to aspects of the present disclosure.
Figure 8:
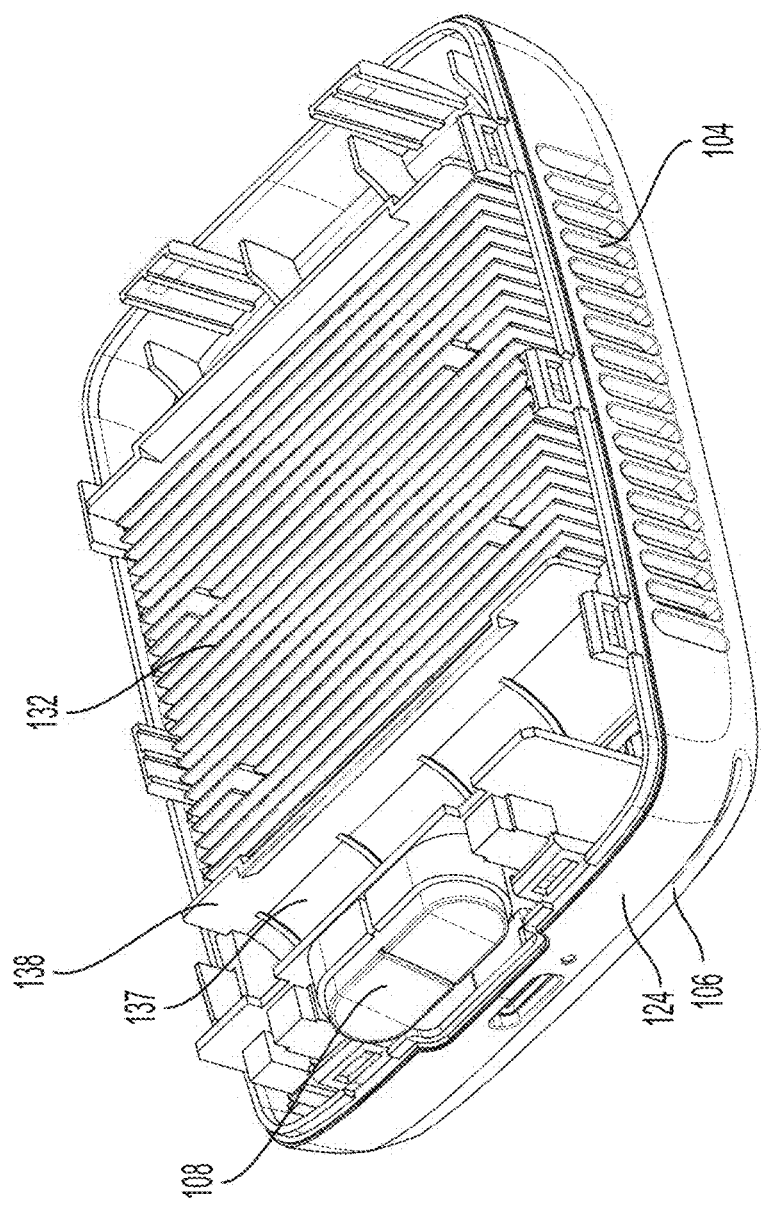

The temperature-controlled device 10 further includes one or more batteries 130 which include at least one battery. In some aspects, the one or more batteries 130 may be one or more rechargeable batteries and may be arranged on one or more sides of the perimeter of the heat sink 132. Referring to FIG. 7, which is a cross-sectional view of FIG. 1, the one or more batteries 130 may include two rechargeable batteries seated on an outer side of a support member 137. The support member 137 may be located inside the housing 100, horizontally off-centered, between the fan 126 and the controllable temperature element 134. The support member 137 may have a square-shaped bottom side on which the heat sink 132 is seated at a middle portion of the support member 137. Two side walls 138 of the support member 137 may extend straightly upward. Each of the two side walls 138 may include a wing portion 139 having a shape for supporting the one or more rechargeable batteries 130 as shown in FIGS. 6-8. In some aspects, one or more side walls of the support member 137 extend as described above to support the corresponding number of rechargeable battery. Accordingly, the support member 137 can support the one or more batteries 130, the heat sink 132, and the fan 126 in a manner that facilitates air flow between the fan 126 to heat spreader 118. Support member 137 is configured to hold the one or more batteries 130 in a horizontally spaced position such that the one or more batteries 130 do not impede air flow within housing 100. In an alternative embodiment, the one or more batteries 130 may be external to the housing 100 and connected to the temperature-controlled device 10 by, for example, a charging cable.

Referring back to FIG. 6, a bottom side of the support member 137 has, at its center, an opening 144 through which the controllable temperature element 134 is fitted to be in contact with the heat sink 132 below the heat sink 132. In addition, the heat spreader 118 may be connected to the bottom side of the support member 137. In some aspects, the opening 144 may be smaller than the heat sink 132 but larger than the controllable temperature element 134. In addition, a padded liner 136 (FIG. 10) having a non-conductive material may be implemented on the second side of the heat spreader 118 inside the housing 100 to protect the controllable temperature element 134 and its surroundings to prevent thermal energy from transferring to unnecessary areas within housing 100, by surrounding the controllable temperature element 134.

The above-described configuration and structure of the internal components can provide a rapid heating and cooling effect to a user through direct contact with the heat spreader 118 while allowing for efficient cooling of the internal components of temperature-controlled device 10. For instance, when a user grasps the temperature-controlled device 10 as shown in FIGS. 11 and 12 for hot or cold therapy, outside air can sufficiently enter the temperature-controlled device 10 through the combination of the air inlet 102 and the undercut 116 by operating the device, and the air can be guided to flow down to the fan 126, the heat sink 132, and finally to outside the housing 100 through the air outlet 104, enabling fast cooling.

In some aspects, the operation (e.g., heating and cooling) of the temperature-controlled device 10 can be controlled by user manipulation of the buttons 108. Referring to FIGS. 7 and 8, the temperature-controlled device 10 may include two or more buttons 108 connected on the PCB 140, where the buttons 108 are on the external surface of the housing 100 for a user to press. The buttons 108 can control turning on and off of the temperature-controlled device 10, changing the control modes, changing temperature settings, etc. Some of the features are controlled by multiple presses of the associated button. In one aspect, one of the buttons 108 may control a heating mode, and the other one of the buttons 108 may control a cooling mode.

More specifically, the buttons 108 may include one button for turning on the temperature-controlled device 10, and the first LEDs 110 may display, e.g., green light, to indicate that the temperature-controlled device 10 is on. The buttons 108 may also include corresponding buttons for activating different modes of the temperature-controlled device 10, such as a button configured to activate (and deactivate) a heating mode and a button configured to activate (and deactivate) a cooling mode. The buttons 108 may be visually distinguishable from each other by icons or colors, e.g., red for heating mode and blue for cooling mode. In addition, two or more buttons of buttons 108 may be configured to be pressed simultaneously to activate a contrast mode. In some aspects, the temperature-controlled device 10 may be configured to detect the length of button presses for the buttons 108. For example, pressing a button for a predetermined period of time (e.g., 2 seconds or less) may cause the temperature-controlled device 10 to switch modes. In some aspects, the predetermined period of time may be different (e.g., shorter or longer) than the period of time needed to press the button for activating a mode or turning on the temperature-controlled device 10.

The heating and cooling modes may be configured with different temperature levels. The heating mode may implement a range of temperature values including predetermined heating thresholds (e.g., above 30° C. but less than 50° C., or alternatively between 35° C. and 43° C.) as a first temperature setting. Examples of discrete values within the range for the heating mode may include, for example, values of 350 C, 39° C., and 43° C. In some other aspects, the temperature range for each mode may vary, such that each range may be greater (e.g., above 20° C. but less than 60° C.) or smaller (e.g., above 38° C. but less than 40° C.).

Similarly, the cooling mode may implement a range of temperate values including a predetermined cooling threshold (e.g., below 20° C., or alternatively between 8° C. and 16° C.) as a second temperature setting. Examples of discrete values within the range for the cooling mode may include, for example, values of 160 C, 12° C., and 8° C. In some aspects, the heating and cooling temperature values of the temperature-controlled device 10 may be specifically chosen to maximize the benefits and safety of treatment directly on users' skin without concern for skin irritation, burns, etc. In some other aspects, the temperature range for each mode may vary, such that each range may be greater (e.g., above 3° C. but less than 30° C.) or smaller (e.g., above 10° C. but less than 18° C.).

The buttons 108 may include one or more buttons for configuring the temperature settings in each mode. In some aspects, the buttons 108 may be configured to activate modes based on a duration of a button press (e.g., a long press for 5 seconds). For example, after activating a desired mode, continuous pressing of the button may result in cycling between different temperature settings until the right temperature setting is selected. The first LEDs 110 may be multi-colored (e.g., bicolor, tricolor) and may indicate the currently selected temperature setting (e.g., a current temperature of the corresponding temperature mode) by displaying each temperature setting in different colors (e.g., blue, orange, red). In some aspects, the first LEDs 110 are configured to display the first temperature setting in the heating mode in a first color, a second LED 114 is configured to display the second temperature setting in the cooling mode in a second color. The first color and the second color may be different colors.

In some aspects, the contrast mode may alternate between the cooling mode and heating mode. The contrast mode may include one or more cycles that alternate between the cooling mode and the heating mode for predetermined time periods. For example, a cooling mode of, e.g., 8° C. may be maintained for a certain period (e.g., 1 min) and then switched to a heating mode of, e.g., of 43° C., for a certain period (e.g., 1 min). The temperature and period settings may be a preset or user configuration settings, e.g., the temperature-controlled device 10 may be configured to communicate with a user device such as a mobile phone or computer. In some aspects, the combination of heating and cooling therapy provided by the temperature-controlled device 10 in contrast mode may be beneficial in helping a user maximize recovery of an area of their body that may be fatigued or sore from activity.

When a desired mode (e.g., cooling, heating, or contrast) is selected by a user, the temperature change can be achieved quickly, e.g., it may take about 2 seconds to drop Δ 15° C., or it may take about 1 second to increase Δ 15° C. This is possible due to the above-described structural arrangement of each element forming, e.g., the air flow path from the air inlet 102 and the undercut 116 as a secondary air inlet to the air outlet 104 passing through the internal components within the housing 100.

Below the first LEDs 110, the housing 100 further includes the charging port 112 connected to and electrically communicating with the PCB 140 to charge the one or more rechargeable batteries 130 (see FIG. 1). The second LED 114 may be located adjacent the charging port 112 and display a charging level in different colors. In some aspects, the buttons 108, the first LEDs 110, the charging port 112, and the second LED 114 are on the shorter side (e.g., width direction) of the housing 100 having a generally cuboid shape, while the air outlet 104 are formed on the longer sides (e.g., length direction) of the housing 100. In addition, one among the pair of recesses 106, which will be described later in detail, is formed below the charging port 112 on the same side of the housing 100 without interfering with any of the control/display elements.

In some aspects, although not limited, the one or more rechargeable batteries 130 may be lithium-ion batteries and may have a battery life about 60 minutes. In some aspects, the batteries 130 may be Nickel Cadmium (Ni—Cd), Nickel Metal Hydride (Ni-MH), Lithium Ion (Li-ion), Lithium Polymer (Li—Po), or other type of rechargeable batteries. In some aspects, batteries 130 may be implemented as disposable batteries. The batteries 130 may be in electric communication with the electronic components, e.g., the fan 126, the controllable temperature element 134, and the PCB 140, via one or more electrical contacts. The batteries 130 may be arranged on one or more sides of the perimeter of the fan 126, the heat sink 132, and the controllable temperature element 134, so as not to interfere with the air flow and thermal transfer through a central path of the internal cavity of the temperature-controlled device 10 (refer to the arrows in FIG. 19). Further and as also described above, the batteries 130 are horizontally spaced apart from each other by the fan 126, the heat sink 132, and the controllable temperature element 134 as well as any internal electronic components so as to form a path within housing 100 through which air may flow.

For example, as shown in FIG. 7, when the temperature-controlled device 10 includes two batteries 130 supported on the support member 137 adjacent the third and fourth surfaces of the lower side cover 124. That is, each battery 130 is seated on the corresponding wing portion 139 located at each outer side of the support member 137. The wing portions 139 are spaced apart from each other such that internal electronic components, such as the fan 126 and the heat sink 132 can be positioned in the space between the wing portions 139 (or the two side walls 138). As described above, such a configuration guides air flow through a path formed within the housing 100 to cool internal components in proximity to the path. This air path formed between the batteries 130 can facilitate air to quickly cool the internal components, etc.

FIGS. 9 and 10 show an internal view and an exploded view of the lower side cover 124, respectively. The lower side cover 124 has a first opening 145, through which the buttons 108, the first LED 110, the charging port 112, and/or the second LED 114 are exposed, on a surface (e.g., third side surface) of the housing 100. The housing 100 further includes a second opening 146 on a bottom surface facing the top surface of the temperature-controlled device 10 such that the heat spreader 118 extends out through the second opening 146. In some aspects, the first and second side surfaces of the housing 100 extending in the length direction may be longer than the third side surface extending in the width direction. As described above, the heat spreader 118 may have a recessed portion 135 to securely receive the controllable temperature element 134. The recessed portion 135 may reduce the weight/cost of the temperature-controlled device 10 by reducing or minimizing the use of unnecessary material.

For instance, referring back to FIG. 7, rather than having a flat surface in a solid body shape, the heat spreader 118 has the recessed portion 135 recessed on the top such that a center portion 119 is configured to protrude from the recessed portion 135 to contact the controllable temperature element 134. The controllable temperature element 134 further includes a padded liner 136 to surround the heat spreader 118 preventing thermal energy from transferring from or to the heat spreader 118 in addition to protecting the heat spreader 118.

FIGS. 11 and 12 illustrate the portable therapeutic temperature-controlled device 10 grasped by a user's hand in various views. In particular, FIG. 12 illustrates that air flow from the air inlet 102 to the air outlet 104 is assured (e.g., the arrows).

Figure 13:
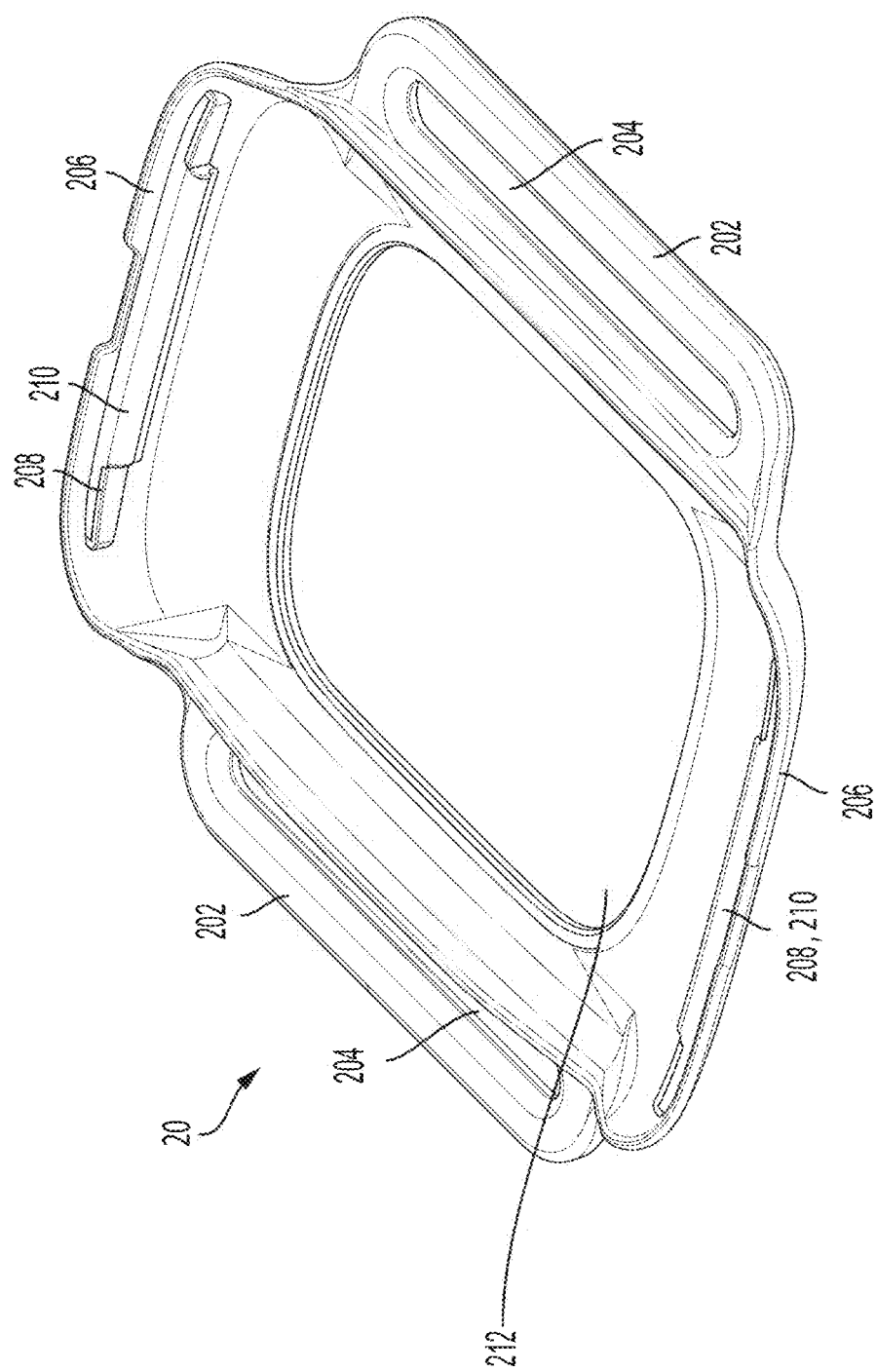
FIG. 13 is a perspective view of a strap case according to aspects of the present disclosure.
Figure 14:
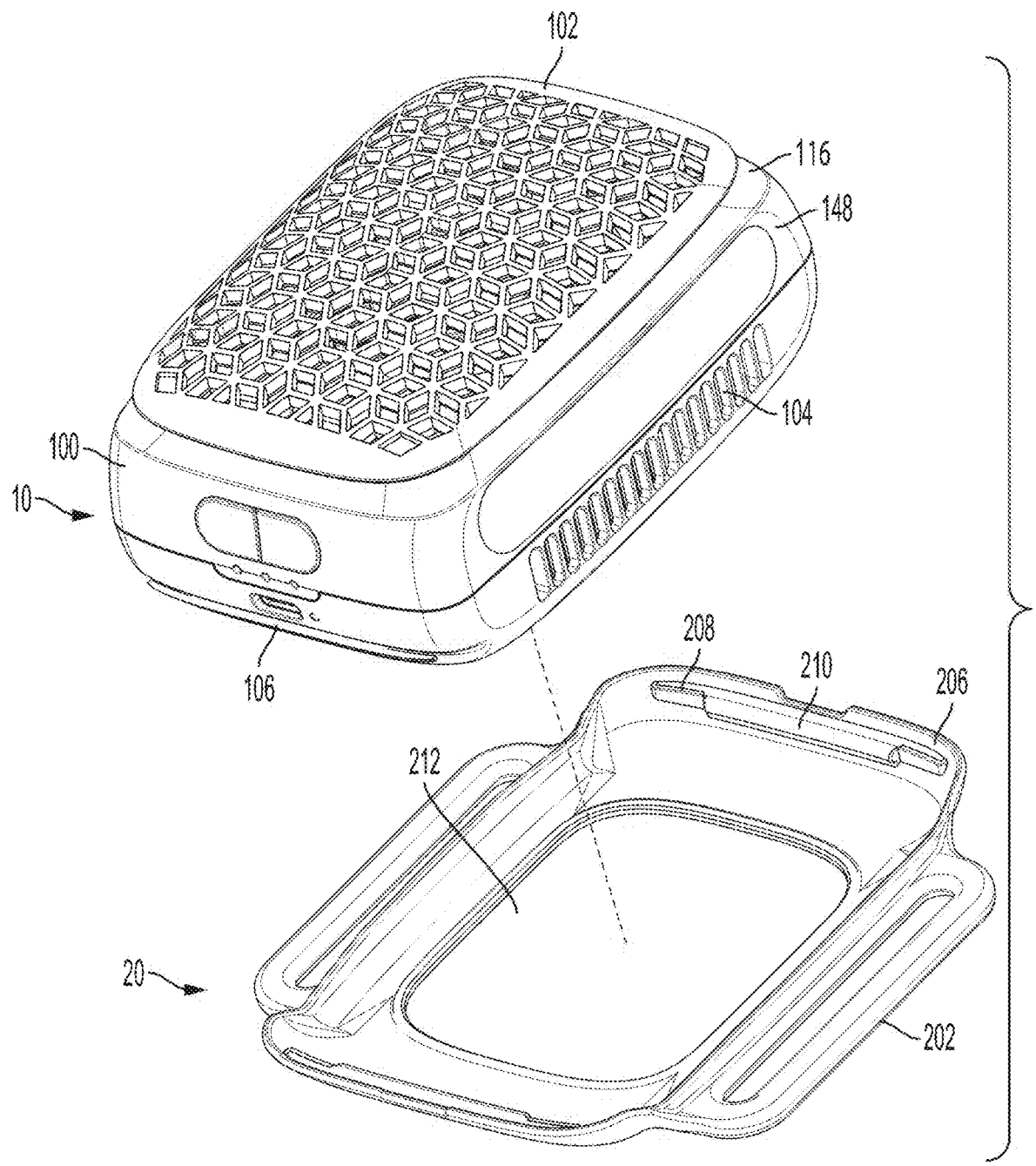
FIG. 14 is a perspective view of the strap case of FIG. 13 and the portable therapeutic temperature-controlled device of FIG. 1.

FIGS. 13 and 14 show a strap case 20 that is designed to receive the temperature-controlled device 10. The strap case 20 is generally formed of a plastic material similar to the housing 100 and has a rectangular shape. In some aspects, the strap case 20 includes a pair of strap buckle portions 202 at opposite sides each having a buckle opening 204, and a pair of side arms 206 curvedly extending upward. Each side arm 206 has a protrusion 208 extending toward a center opening 212 to snap-fit to the respective recess 106 of the housing 100. In addition, the pair of strap buckle portions 202 may integrally extend away from the center opening 212 in a width direction. Accordingly, the strap case 20 can receive the temperature-controlled device 10 by engaging the protrusion 208 with the respective recess 106. Each protrusion 208 on the pair of side arms 206 is provided with a padded layer 210 thereon to protect the friction between the protrusion 208 and the recess 106. The padded layer 210 may be formed of a silicone material (including thermoplastic silicone, thermoset silicone, and silicone gels) or a rubber material for preventing wear and scratch between the protrusion 208 with the respective recess 106 when assembling and disassembling. In some other aspects, a plastic material may be used for the padded layer 210 using rough textures thereon.

Figure 15:
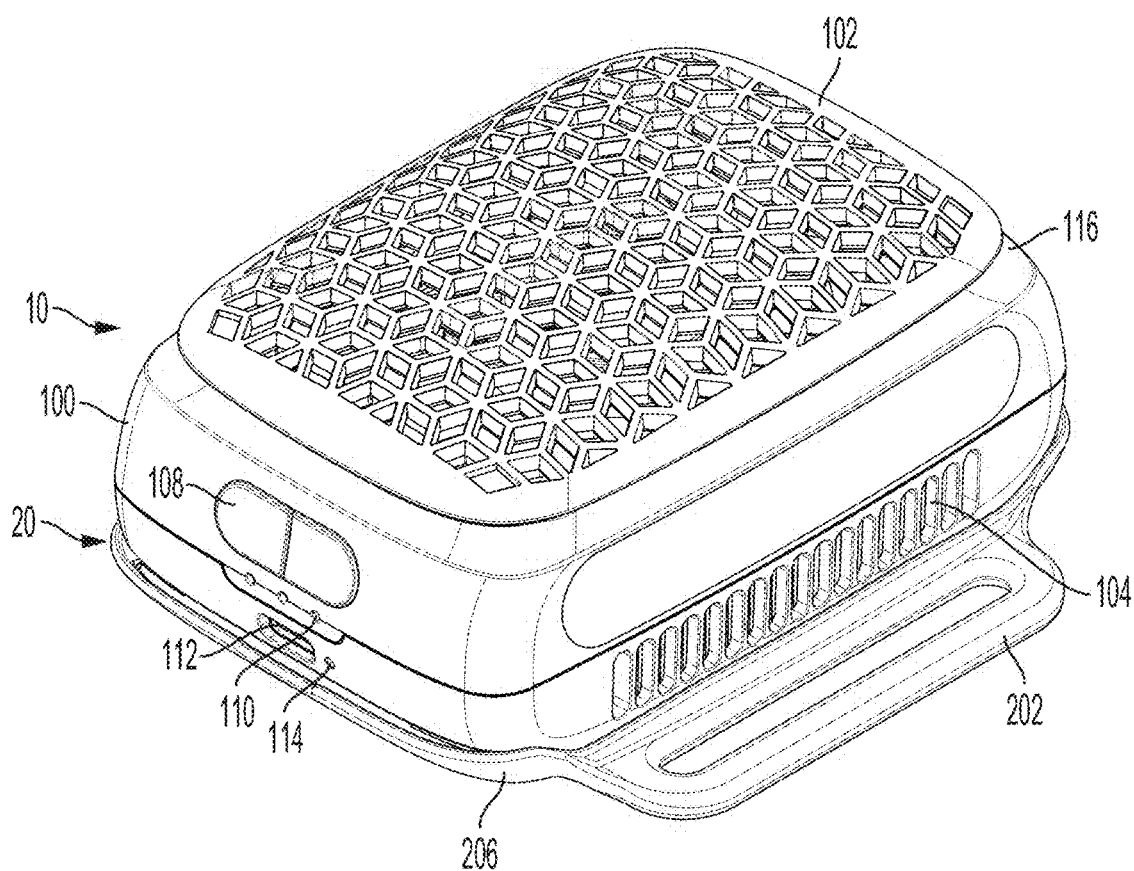
FIG. 15 is a perspective view of the strap case and the portable therapeutic temperature-controlled device as assembled.
Figure 16:
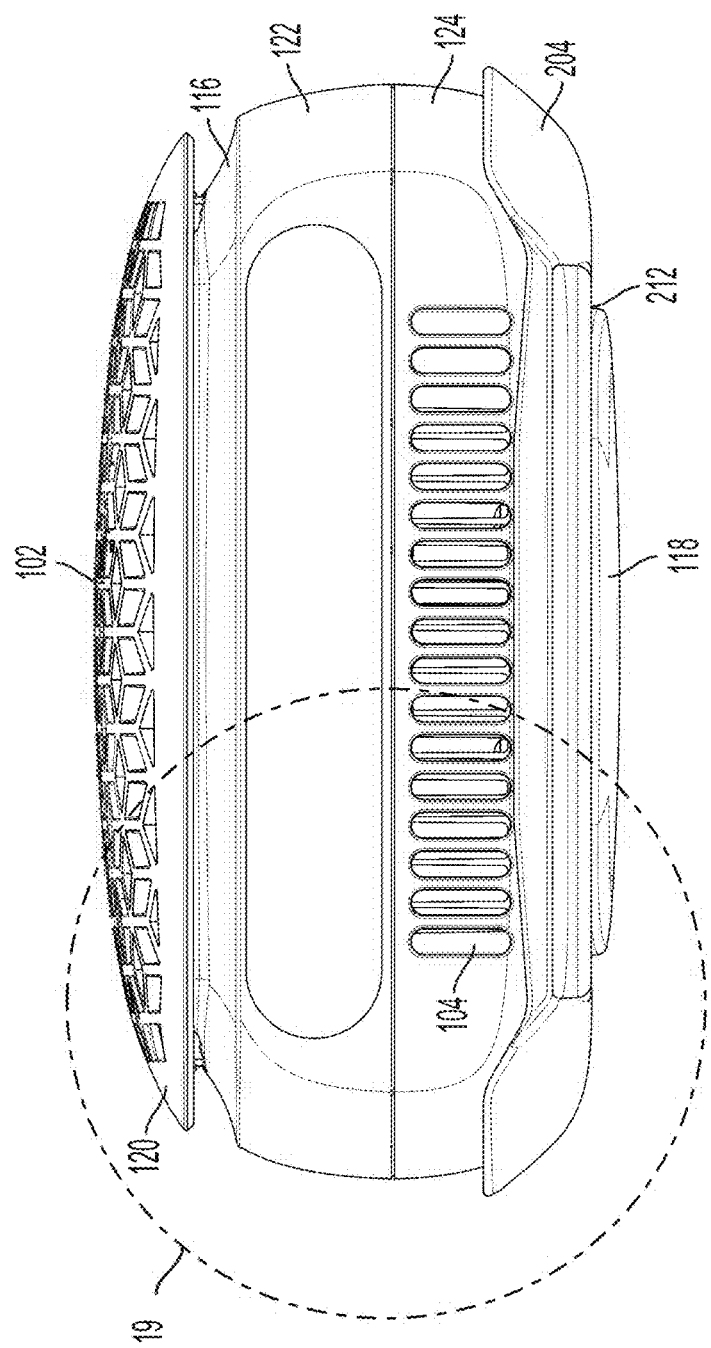
FIG. 16 is a side view of the strap case and the portable therapeutic temperature-controlled device as assembled.
Figure 17:
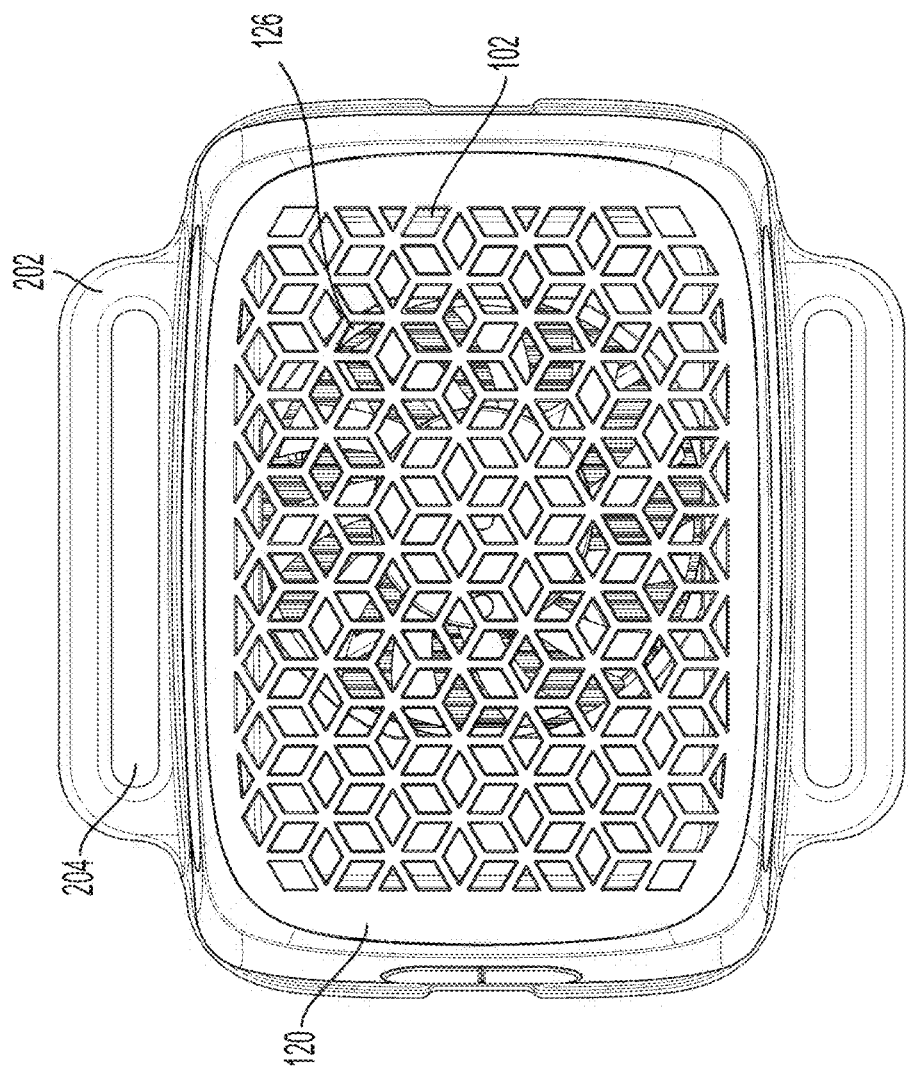
FIG. 17 is a top view of the strap case and the portable therapeutic temperature-controlled device as assembled.
Figure 18:
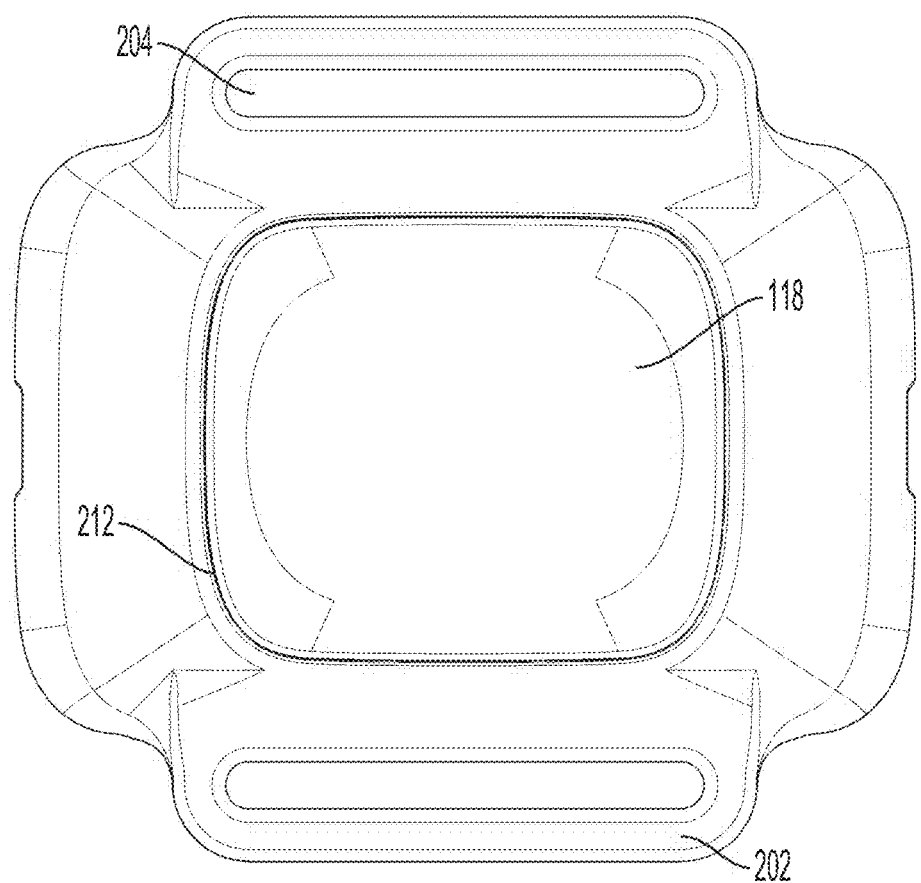
FIG. 18 is a bottom view of the strap case and the portable therapeutic temperature-controlled device as assembled.

FIGS. 15-19 show an assembly of the strap case 20 and the temperature-controlled device 10 in various views. As shown in FIG. 15, when the strap case 20 and the temperature-controlled device 10 are assembled, the air inlet 102 and the air outlet 104 are fully exposed. In addition, referring to FIG. 16 as well as FIG. 14, the heat spreader 118 extends on a bottom side of the strap case 20 through the center opening 212 of the strap case 20 to assure the first contact to a user's body. FIG. 17 shows a top view of the assembly of the strap case 20 and the temperature-controlled device 10, and FIG. 18 shows a bottom view of the assembly. As shown, the top cover 120 includes a plurality of openings forming the air inlet 102 allowing air to enter by the help of the fan 126.

Figure 19:
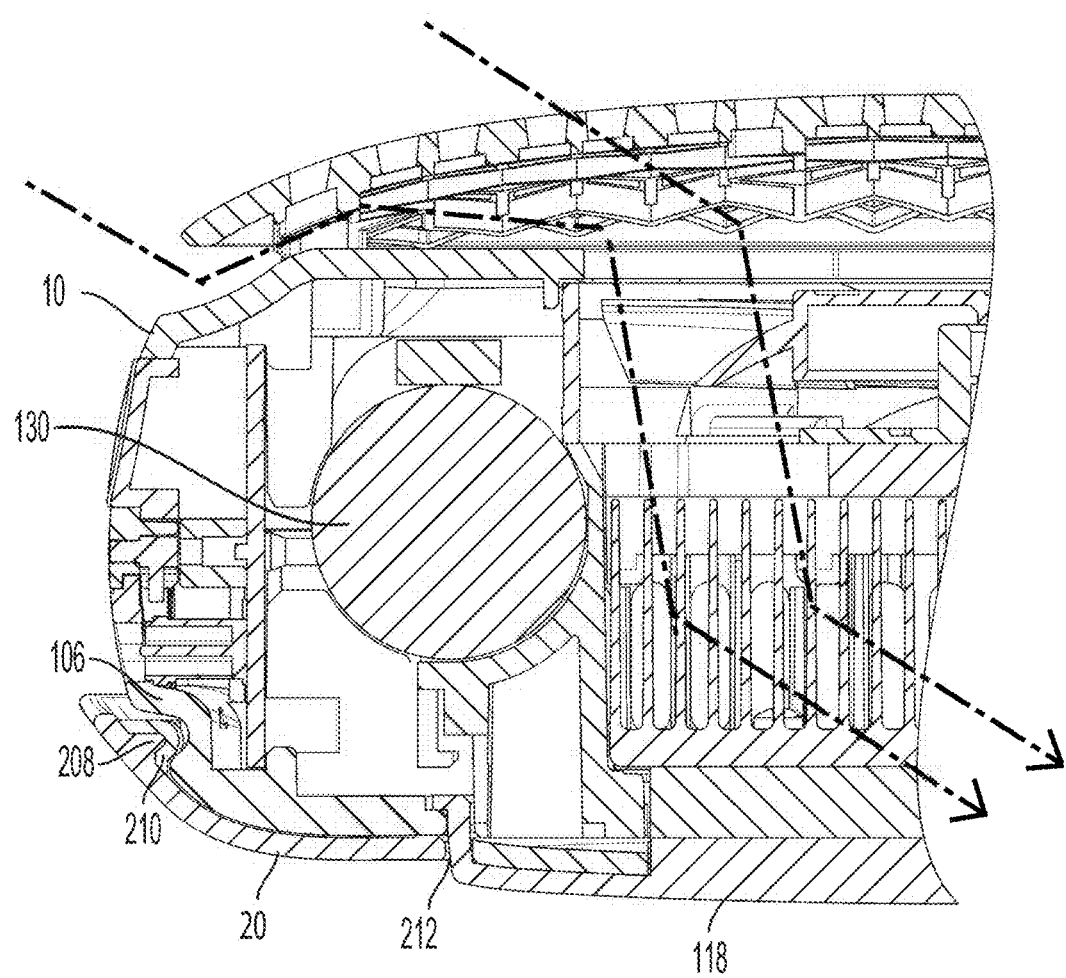
FIG. 19 illustrates a magnified cross-section view of FIG. 16.

FIG. 19 is a magnified cross-sectional view of FIG. 16 where the strap case 20 and the temperature-controlled device 10 are snap-fitted by the respective protrusion 208 and the recess 106, with the padded layer 210 protecting the contact portion as well as securing the connection between the strap case 20 and the temperature-controlled device 10. In addition, the battery 130 may be horizontally spaced apart from any internal electronic and metallic components of the temperature-controlled device 10. This arrangement allows air flow (the arrows in FIG. 19) to enter the temperature-controlled device 10 and exiting the temperature-controlled device 10 without being blocked by the battery 130, as also described above.

FIGS. 20A, 20B, 21A, 21B, 22A, 22B, 23A, and 23B illustrate a strap system for the assembly of the temperature-controlled device 10 and the strap case 20.

Figure 20A:
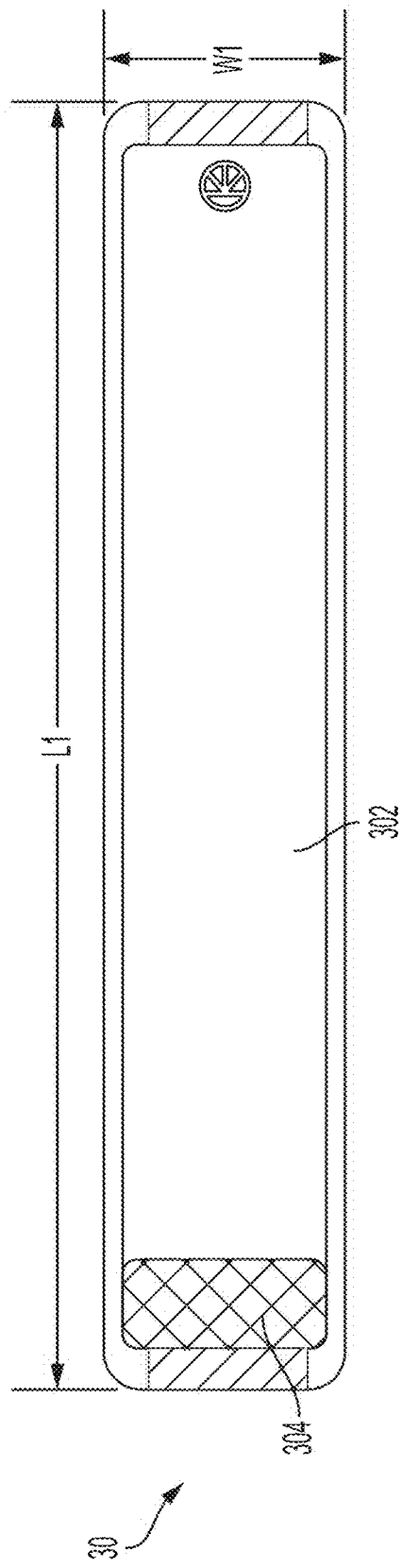
FIGS. 20A and 20B are top and bottom views of a primary strap according to aspects of the present disclosure.
Figure 20B:
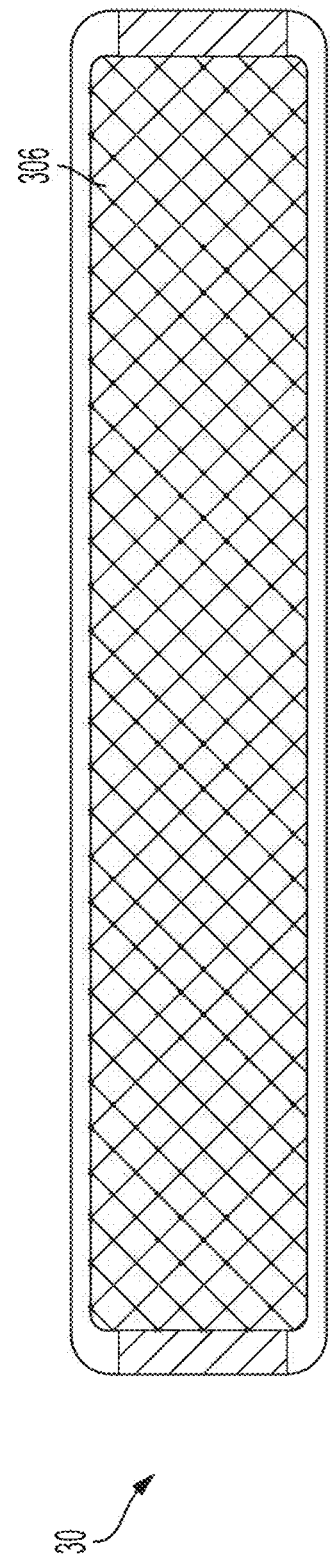

Referring to FIGS. 20A and 20B, the strap system includes a primary strap 30 having a neoprene material 302 on one side or a first side (FIG. 20A) along the entire length and a first hook and loop material 306 (e.g., Velcro) on the entire length of the opposite side or a second side (FIG. 20B). On the neoprene material 302, a second hook and loop material 304 may be partially provided at one end. The primary strap 30 has a first length approximately, e.g., 100 cm (L1) and a first width approximately, e.g., 6 cm (W1), and can be fit through the buckle openings 204 of the strap buckle portions 202. For instance, each end of the primary strap 30 can be inserted through the buckle opening 204 and folded over such that the first hook and loop material 306 can be fastened to each other, as shown in FIGS. 21A and 21B. When the temperature-controlled device 10, the strap case 20, and the primary strap 30 are assembled together, the assembly is configured to strap on a user such that heating and cooling of the controllable temperature element 134 are selectively transferred to the user's body part that is in contact with the heat spreader 118.

Figure 22A:
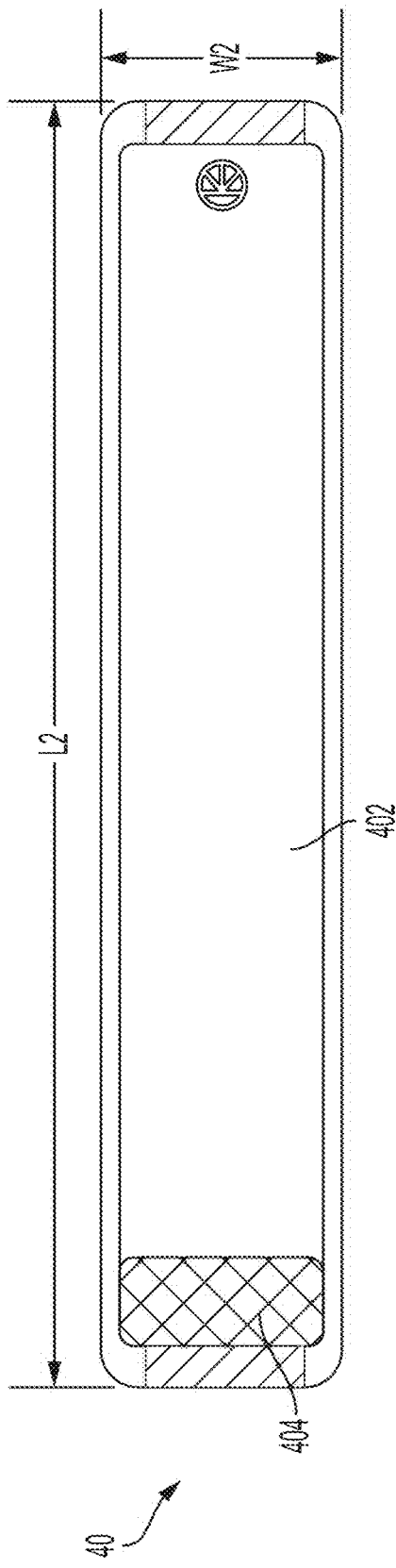
FIGS. 22A and 22B are top and bottom views of a secondary strap according to aspects of the present disclosure.
Figure 22B:
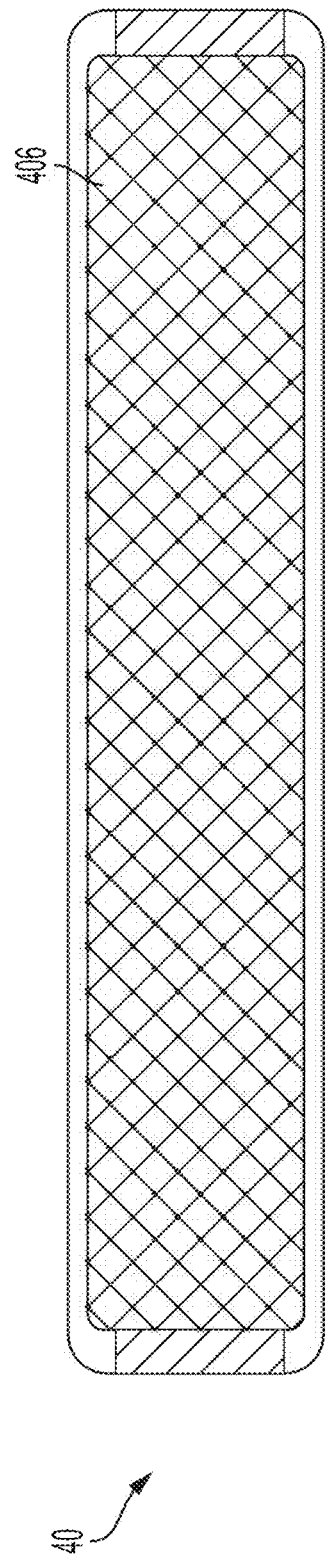
Figure 23A:
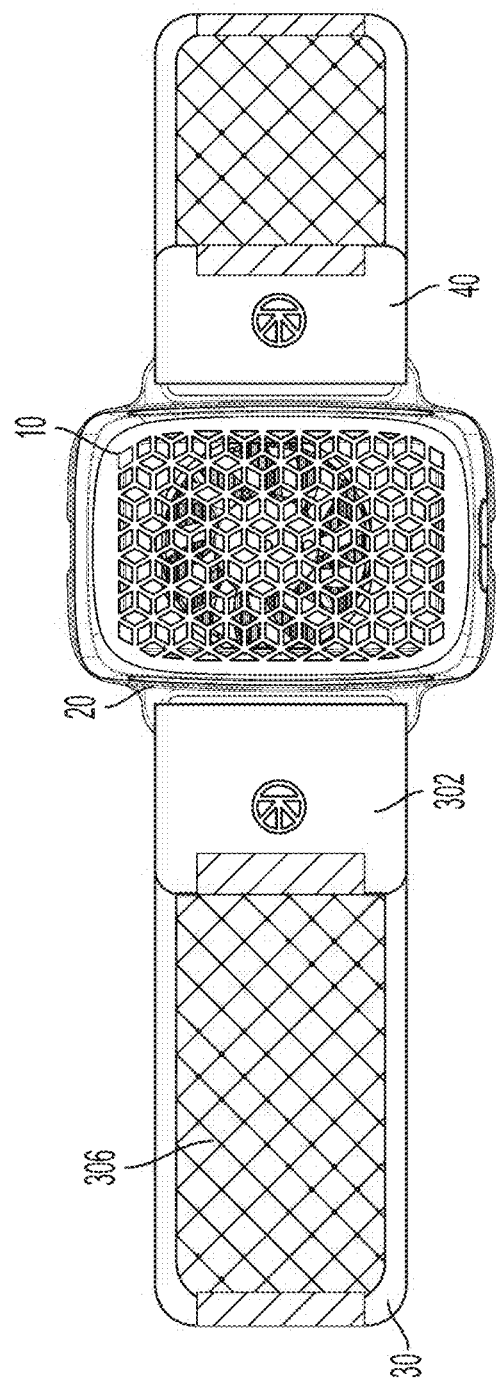
FIGS. 23A and 23B are top and side views of the portable therapeutic temperature-controlled device assembled with the primary strap and the secondary strap.
Figure 23B:
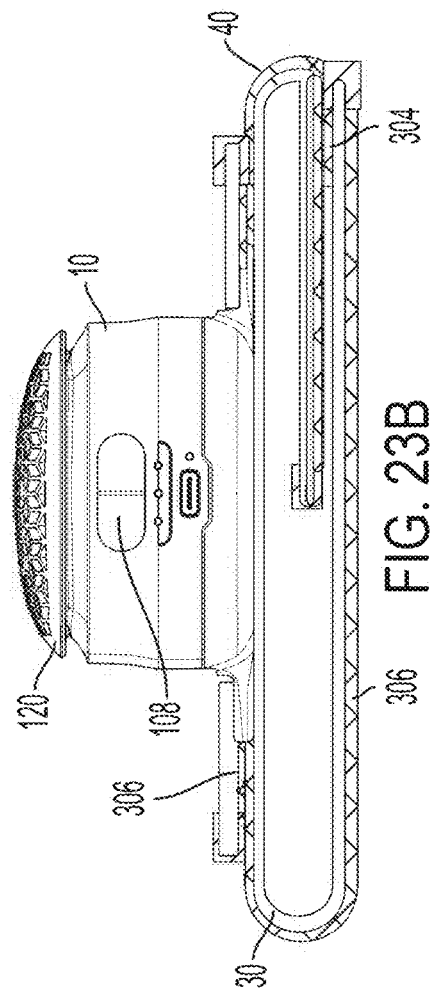

Additionally, with reference to FIGS. 22A and 22B, the strap system includes a secondary strap 40 having a shorter length, e.g., a second length approximately 60 cm (L2) and a second width approximately 6 cm (W2). The secondary strap 40 can be connected to the primary strap 30 to form one long strap system as shown in FIGS. 23A and 23B. Similar to the primary strap 30, the secondary strap 40 may include a neoprene material 402 on a first side of the secondary strap 40 and a third hook and loop material 406 on the entire length of the opposite side. On the neoprene material 402, a fourth hook and loop material 404 is partially provided at one end. The secondary strap 40 can be fit through the buckle openings 204 of the strap buckle portions 202. For instance, each end of the secondary strap 40 can be fit through the buckle opening 204 and folded over such that the third hook and loop material 406 can be fastened to each other. The dimensions of the primary and secondary straps 30, 40 described herein are merely exemplary values and thus not limited thereto.

Alternatively, the secondary strap 40 can be coupled to the one end of the primary strap 30 by fastening the second hook and loop material 304 as a first fastening mechanism and the third hook and loop material 406 as a second fastening mechanism. That is, the adjustable strap system, using the primary strap 30 or secondary strap 40 individually, or together, allows versatile use. For instance, for use on a person with a bigger figure vs. a smaller figure, or strap around the shoulder or back vs. strap around a wrist or ankle, etc.

In some instances, the user may desire to apply heating and/or cooling effects to small areas on the user's body. For example, the user may desire to apply heating and/or cooling effects to a facial region of the user. More specifically, the user may desire to apply heating and/or cooling effects to a forehead, temple, cheek, eye, chin, lip, neck, etc., of the user's facial region. In such instances, the user may prefer to apply the heating and/or cooling effects with a device that has a small profile. For example, the user may prefer to use a device that is similar in size to a lipstick container, a lip balm container, a pack of gum, etc., which can fit easily into a pocket, handbag, purse, etc. In some instances, the user may also prefer to use a device with a contoured or angled surface area that can effortlessly be applied to treat particular portions of the user's facial region with heating and/or cooling effects. Aspects described with respect to FIGS. 24-27 refer to a device that can satisfy preferences of a user to have a device for heating and/or cooling that has a small profile and can be easily stowed.

Figure 24:
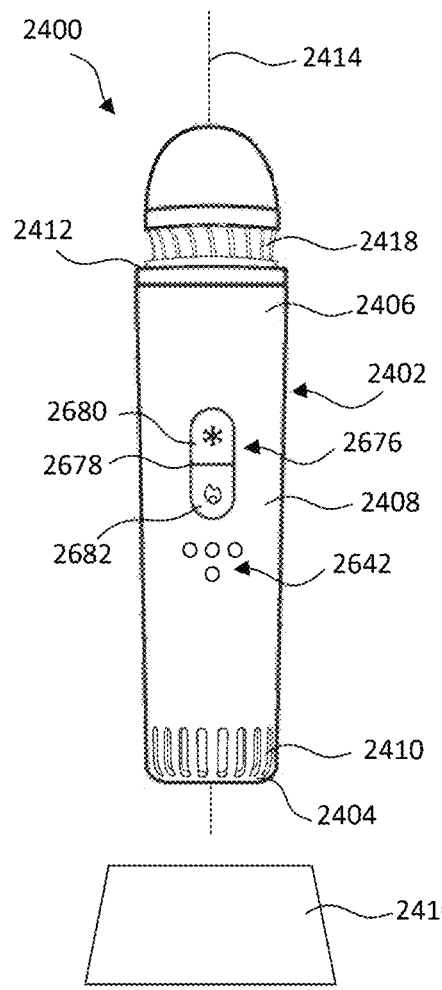
FIG. 24 is a side view of a portable therapeutic temperature-controlled device according to aspects of the present disclosure.

FIG. 24 is a side view of a temperature-controlled device 2400 according to aspects of the present disclosure. In some aspects, the temperature-controlled device 2400 can be smaller than the temperature-controlled device 10. For example, the temperature-controlled device 2400 can comprise at least one dimension that is smaller than a corresponding dimension of the temperature-controlled device 10. The temperature-controlled device 2400 can comprise at least one surface area that is smaller than a corresponding surface area of the temperature-controlled device 10. The temperature-controlled device 2400 can comprise a volume that is smaller than a corresponding volume of the temperature-controlled device 10.

In some aspects, the temperature-controlled device 2400 can comprise a housing 2402. In some aspects, the housing 2402 can comprise a symmetric shape. For example, the housing 2402 can comprise a cylindrical shape, a rectangular shape, etc. In some aspects, the housing 2402 can comprise an asymmetric shape. The housing 2402 can comprise a first end 2404 located opposite a second end 2406, and a wall 2408 extending between the first end 2404 and the second end 2406. In some aspects, the housing 2402 can define a longitudinal axis 2414 that extends between the first end 2404 and the second end 2406. In some aspects, the housing 2402 can define an air inlet 2412 located at the second end 2406 and configured to permit air to flow into the housing 2402. In some aspects, the housing 2402 can define an air outlet 2410 located at the first end 2404 and in fluid communication with the air inlet 2412. The air outlet 2410 can be configured to permit air to flow out of the housing 2402. The housing 2402 may include a display 2676 located on the wall 2408 of the housing 2402, in which the display 2676 includes a button arrangement 2678 comprising a first button 2680 and a second button 2682, and a light arrangement 2642. The display 2676 is further described with reference to FIG. 26B.

In some aspects, the housing 2402 is configured to at least partially cover components of the temperature-controlled device 2400. For example, the temperature-controlled device 2400 can comprise a fan, a heat sink, and a controllable temperature element that can be at least partially covered by the housing 2402. As shown in FIG. 24, a portion of a heat sink 2418 can be partially covered by the housing 2402, and a portion of the heat sink 2418 can be located outside of the housing 2402. The components of the temperature-controlled device 2400 that can be at least partially covered by the housing 2402 are further described with respect to FIG. 27.

In some aspects, the temperature-controlled device 2400 can comprise a heat spreader 2420. The heat spreader 2420 can be aligned with the longitudinal axis 2414 and can be located outside of the housing 2402. In some aspects, the heat spreader 2420 can be located closer to the second end 2406 of the housing 2402 than the first end 2404 of the housing 2402. The heat spreader 2420 can be configured to increase in temperature or decrease in temperature in response to a temperature change of the controllable temperature element (shown and described in FIG. 27). For example, in some aspects the heat spreader 2420 can be configured to receive thermal energy from the controllable temperature element. In some aspects, the heat spreader 2420 can be in physical contact with the controllable temperature element such that heating or cooling from the controllable temperature element can be transferred to the heat spreader 2420 via conduction. In some aspects, the heat spreader 2420 may not be in physical contact with the controllable temperature element, and the heating or cooling from the controllable temperature element can be transferred to the heat spreader 2420 via convection and/or radiation.

In some aspects, the first end 2404 can be received in a battery charger 2416 to charge a battery located in the housing 2402. In such aspects, a first electrical contact can extend from the battery to an outer surface of the housing 2402 at the first end 2404 such that, when the first electrical contact contacts a second electrical contact of the battery charger 2416, power can flow to the battery to charge the battery. In other embodiments, the first end 2404 may include a charging port (e.g., a USB charging port) for charging the battery located in the housing 2402.

Figure 25:
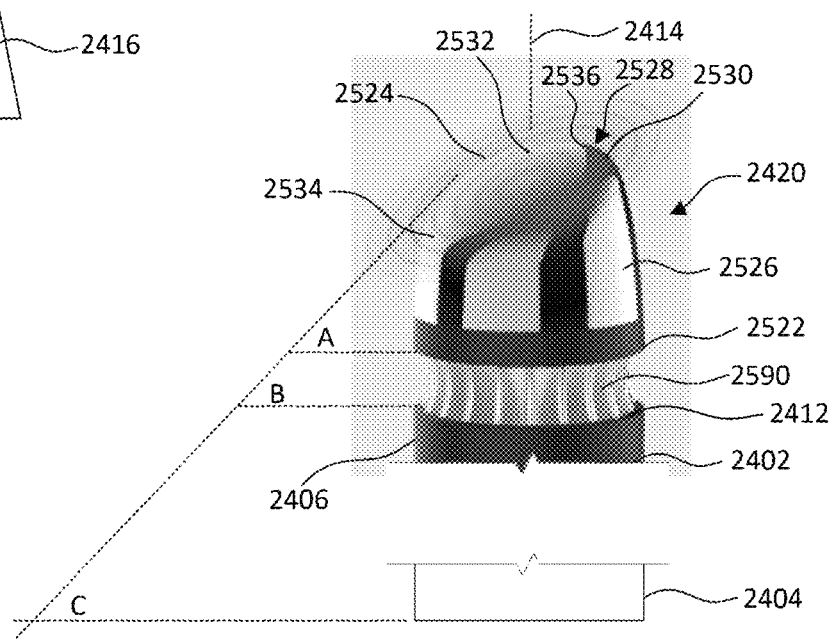
FIG. 25 is a side view of a spreader of the portable therapeutic temperature-controlled device of FIG. 24 according to aspects of the present disclosure.

FIG. 25 is a side view of the heat spreader 2420 according to aspects of the present disclosure. In some aspects, the heat spreader 2420 can comprise a bottom surface 2522 located opposite a top surface 2524. The heat spreader 2420 can comprise an outer surface 2526 that extends between the bottom surface 2522 and the top surface 2524. In some aspects, the top surface 2524 can be configured to contact the face of the user. In such aspects, the top surface 2524 can be referred to as the contact surface. In some aspects, the top surface 2524 and the outer surface 2526 can be configured to contact the face of the user. In such aspects, both the top surface 2524 and the outer surface 2526 can be referred to as the contact surface. In some aspects, the outer surface 2526 can be configured to contact the face of the user. In such aspects, the outer surface 2526 can be referred to the contact surface.

In some aspects, the heat spreader 2420 can comprise a frustoconical shape. For example, the bottom surface 2522 can comprise a circular cross-sectional shape (for example, when viewed along the longitudinal axis 2414) and the outer surface 2526 can extend between the bottom surface 2522 and the top surface 2524 at an acute angle relative to the bottom surface 2522. In some aspects, the top surface 2524 and the bottom surface 2522 can be approximately parallel to each other. In aspects where the bottom surface 2522 and the top surface 2524 are approximately parallel to each other, the top surface 2524 can comprise a circular cross-sectional shape, and the circular cross-sectional shape of the bottom surface 2522 can be larger than the circular cross-sectional shape of the top surface 2524. Stated differently, the outer surface 2526 can extend from the bottom surface 2522 to the top surface 2524 along the longitudinal axis 2414 in a direction away from the second end 2406 of the housing 2402 at an acute angle relative to the bottom surface 2522.

In some aspects, the top surface 2524 and the bottom surface 2522 are oriented at an angle to each other. Stated differently, in some aspects the heat spreader 2420 can comprise a frustoconical shape with an angled top surface. More specifically, in some aspects the top surface 2524 can be oriented at a nonzero angle A relative to the bottom surface 2522 (for example, the top surface 2524 and the bottom surface 2522 are not approximately parallel). In some aspects, the top surface 2524 can be oriented at a nonzero angle B relative to the second end 2406 of the housing 2402. In some aspects, the top surface 2524 can be oriented at a nonzero angle C relative to the first end 2404 of the housing 2402. In some aspects, the nonzero angles A, B, or C can be approximately equal. In some aspects, at least two of the nonzero angles A, B, or C can be approximately equal. In some aspects, the nonzero angles A, B, and C can be different from each other. In some aspects, the nonzero angles A, B, and C can be greater than or equal to 5 degrees and less than or equal to 50 degrees. In some aspects, the nonzero angles A, B, and C can be greater than or equal to 10 degrees and less than or equal to 45 degrees. In some aspects, the nonzero angles A, B, and, C can be greater than or equal to 15 degrees and less than or equal to 40 degrees.

In some aspects, the heat spreader 2420 can comprise other shapes. For example, the heat spreader 2420 can comprise a right cylindrical shape. More specifically, the top surface 2524 and the bottom surface 2522 can be approximately parallel to each other, and the outer surface 2526 can extend from the bottom surface 2522 to the top surface 2524 at an angle approximately perpendicular to the bottom surface 2522. As another example, the heat spreader 2420 can comprise an oblique cylindrical shape. More specifically, the outer surface 2526 can extend between bottom surface 2522 and the top surface 2524 at an angle approximately perpendicular to the bottom surface 2522, and the top surface 2524 can be oriented at an angle relative to the bottom surface 2522. As yet another example, the heat spreader 2420 can comprise a round-top cylindrical shape. More specifically, the outer surface 2526 can extend between bottom surface 2522 and the top surface 2524 at an angle approximately perpendicular to the bottom surface 2522, and the top surface 2524 can comprise a curved or convex shape. The top surface 2524 can comprise an apex at a center of the top surface 2524, where the center is further from the bottom surface 2522 than any other point on the top surface 2524. As another example, the heat spreader 2420 can comprise an oblique cylindrical shape. More specifically, the top surface 2524 and the bottom surface 2522 can be approximately parallel to each other, and the outer surface can extend between bottom surface 2522 and the top surface 2524 at an angle such that the top surface 2524 and the bottom surface 2522 are offset relative to the longitudinal axis 2414.

In some aspects, the top surface 2524 and the outer surface 2526 meet at a transition region 2528. In some aspects, the transition region 2528 can follow a curved path between the top surface 2524 and the outer surface 2526. In some aspects, the transition region can comprise a first radius of curvature 2530 where an uppermost portion 2532 of the top surface 2524 meets the outer surface 2526. The uppermost portion 2532 of the top surface 2524 can be the portion of the top surface 2524 that is located furthest from the second end 2406 of the housing 2402 along the longitudinal axis 2414. In some aspects, the transition region can comprise a second radius of curvature 2534 where a remainder of the top surface 2524 meets the outer surface 2526. In some aspects, the first radius of curvature 2530 and the second radius of curvature 2534 are approximately equal. In some aspects, the second radius of curvature 2534 is greater than the first radius of curvature 2530. In aspects where the second radius of curvature 2534 is greater than the first radius of curvature 2530, the uppermost portion 2532 can converge at a tip 2536.

In some aspects, the heat spreader 2420 can be configured to contact the face of the user to heat and/or cool portions of the face of the user. In some aspects, the face of the user can be contacted with the top surface 2524. In such aspects, the temperature-controlled device 2400 can be oriented at an angle relative to the face of the user based on the angle of the top surface 2524. In some aspects, the longitudinal axis 2414 of the temperature-controlled device 2400 can be oriented at an angle approximately equal to one or more of the angles A, B, or C when the top surface 2524 of the heat spreader 2420 is in contact with the face of the user.

In some aspects, various surfaces of the heat spreader 2420 can be configured to contact the face of the user to heat and/or cool portions of the face of the user. In some aspects, the face of the user can be contacted with the outer surface 2526 to heat and/or cool the face of the user. More specifically, the heat spreader 2420 can be configured to distribute the heating and cooling from the controllable temperature element approximately equally across the top surface 2524 and the outer surface 2526. Stated differently, when the controllable temperature element generates heating and cooling, a temperature of the top surface 2524 can be approximately equal to a temperature of the outer surface 2526.

In some aspects, the housing 2402 can comprise an indicator 2590 located below the heat spreader 2420 in the second end of the housing 2402. In some aspects, the indicator 2590 can be configured to indicate a mode selected by the user (e.g., a heating mode, a cooling mode, etc.). For example, in some aspects the indicator 2590 can comprise one or more LED lights located below the air inlet 2412 and adjacent to the heat sink 2418, and the indicator 2590 can be configured to illuminate based on the mode selected by the user. More specifically, the indicator 2590 can be configured to illuminate in a first color that corresponds to the heating mode and a second color that corresponds to the cooling mode. In some aspects, the indicator 2590 may illuminate at different intensity or power levels corresponding to different settings of heating/cooling temperatures selected by the user.

In some aspects, the indicator 2590 may illuminate at a first intensity level when a first temperature setting is selected, a second intensity level when a second temperature setting is selected, and a third intensity level when a third temperature setting is selected. The increase in intensity levels may correspond to an increase in brightness of the indicator 2590 to show the changes in temperature for controlling the heat sink 2418. In some aspects, the indicator 2590 may flash or blink a predetermined number of times to indicate when different temperature settings for heating/cooling have been selected. In some aspects, the indicator 2590 may flash once at a first temperature setting, twice at a second temperature setting, or three times at a third temperature setting.

Arranged as described, the temperature-controlled device 2400 provides a versatile, small profile heating and cooling accessory for the user. The user can heat and cool different portions of the face of the user using various surfaces of the heat spreader 2420. For example, the user can heat and cool the forehead of the user by placing the top surface 2524 in contact with the forehead. In some aspects, the user can heat and cool an orbital region near an eye of the user by placing the tip 2536 in contact with the orbital region. In some aspects, the user can heat and cool a cheek of the user by placing the outer surface 2526 in contact with the cheek of the user. The examples provided are non-limiting, and various portions of the heat spreader 2420 can be used to heat and cool various portions of the face of the user.

Figure 26A:
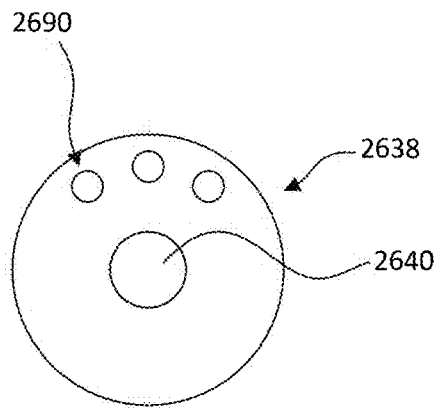
FIG. 26A is a front view of a display of the portable therapeutic temperature-controlled device of FIG. 24 according to aspects of the present disclosure.

FIG. 26A is a front view of a display 2638 of the temperature-controlled device 2400 according to aspects of the present disclosure. In some aspects, the display 2638 can be configured to indicate a temperature setting of the temperature-controlled device 2400. In some aspects, the display 2638 can be configured to turn the temperature-controlled device 2400 on and off. In some aspects, the display 2638 can be located on the wall 2408 of the housing 2402, in between the first end 2404 and the second end 2406 of the housing 2402.

In some aspects, the display 2638 can comprise a button 2640. In some aspects, the button 2640 can be actuated by the user to turn the temperature-controlled device 2400 on and off. In some aspects, the button 2640 can be illuminated by a light when the temperature-controlled device 2400 is turned on. In some aspects, once the temperature-controlled device 2400 is on, the user can actuate the button 2640 to control a temperature setting of the temperature-controlled device 2400. For example, pressing the button 2640 once can turn on the temperature-controlled device 2400. After the temperature-controlled device 2400 is on, pressing the button 2640 two or more times in succession can control the heating and cooling of the heat spreader 2420. Another single press of the button 2640 can turn the temperature-controlled device 2400 off. In some aspects, a predetermined number of presses of the button 2640 can initiate a locking and unlocking function of the temperature-controlled device 2400 to prevent the device from accidentally turning on when not in use or during transport. In some aspects, the predetermined number of presses of the button 2650 may be configured to be detected within a predetermined time period (e.g., three button presses within five seconds). In some embodiments, the button 2640 may be a single button 2640 used to control both heating and cooling of the heat spreader 2420, or alternatively, two buttons 2640 for separately controlling heating and cooling, respectively, of the heat spreader 2420. In some aspects, the display 2638 can be a touchscreen display such that the features described above can be present on the touchscreen.

In some aspects, the display 2638 can comprise a light arrangement 2690. In some aspects, the light arrangement 2690 can comprise a single light. In some aspects, the light arrangement 2690 can comprise two or more lights. In some aspects, a color of the light arrangement 2690 can correspond to a heating mode. In some aspects a color of the light arrangement 2690 can correspond to a cooling mode. In some aspects, the light arrangement 2690 can be configured to emit light having a first color when the heating mode is selected and to emit light having a second color that is different from the first color when the cooling mode is selected. In aspects where the light arrangement 2690 comprises two or more lights, a number of lights illuminated can correspond to a temperature setting. As an example, the light arrangement 2690 can include three lights. At a low temperature setting, one of the three lights can be illuminated. At a medium temperature setting, two of the three lights can be illuminated. At a high temperature setting, all three lights can be illuminated.

Figure 26B:
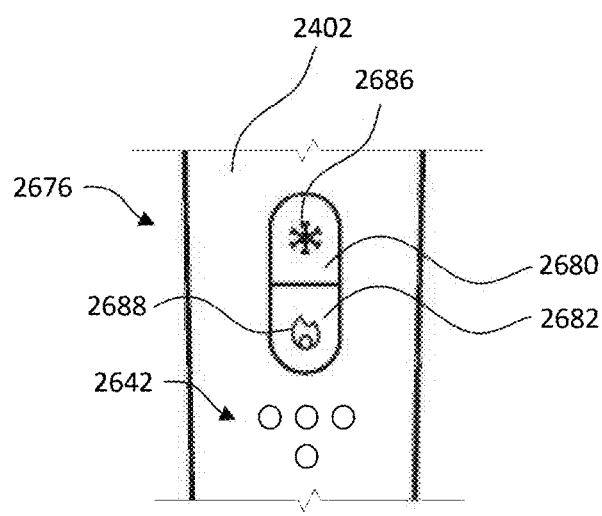
FIG. 26B is a front view of a display of the portable therapeutic temperature-controlled device of FIG. 24 according to aspects of the present disclosure.

FIG. 26B is a front view of the display 2676 of the temperature-controlled device 2400 according to aspects of the present disclosure. In some aspects, the display 2676 may be an alternative embodiment of the display 2638 shown in FIG. 26A. In some aspects, the display 2676 can be located on the wall 2408 of the housing 2402. In some aspects, the display 2676 can be configured to indicate a temperature setting of the temperature-controlled device 2400. In some aspects, the display 2676 can be configured to turn the temperature-controlled device 2400 on and off.

In some aspects, the display 2676 can comprise the button arrangement 2678. In some aspects, the button arrangement 2678 can comprise the first button 2680 and the second button 2682. In some aspects, the button arrangement 2678 can comprise more or fewer buttons (for example, just one button, three buttons, four buttons, etc.). In some aspects, the first button 2680 and second button 2682 may be configured to turn the temperature-controlled device 2400 on and off and activate modes based on a duration of a button press (e.g., a long press for 5 seconds). In some aspects, the first button 2680 can correspond to a cooling mode. In some aspects, the first button 2680 can comprise an icon 2686 that corresponds to the cooling mode. For example, the icon 2686 can comprise an image of a snowflake. In some aspects, the icon 2686 can be illuminated by a light when the cooling mode is initiated. In some aspects, the cooling mode of the temperature-controlled device 2400 can be initiated, stopped, or changed, by actuating the first button 2680. For example, the cooling mode can be initiated by actuating the first button 2680 one or more times. As another example, different cooling mode settings can be initiated by actuating the first button 2680 one or more times. More specifically, the temperature-controlled device 2400 can comprise multiple cooling settings (e.g., the temperature-controlled device 2400 can reach a first temperature at a first cooling setting, the temperature-controlled device 2400 can reach a second temperature at a second cooling setting, the temperature-controlled device 2400 can reach a third temperature at a third cooling setting, etc.), where the cooling settings can be reached by pressing the first button 2680 one or more times.

In some aspects, the second button 2682 can correspond to a heating mode. In some aspects, the second button 2682 can comprise an icon 2688 that corresponds to the heating mode. For example, the icon 2688 can comprise an image of heating waves, a flame, etc. In some aspects the icon 2688 can be illuminated by a light when the heating mode is initiated. In some aspects, the heating mode of the temperature-controlled device 2400 can be initiated, stopped, or changed, by actuating the second button 2682. For example, the heating mode can be initiated by actuating the second button 2682 one or more times. As another example, different heating mode settings can be initiated by actuating the second button 2682 one or more times. More specifically, the temperature-controlled device 2400 can comprise multiple heating settings (e.g., the temperature-controlled device 2400 can reach a first temperature at a first heating setting, the temperature-controlled device 2400 can reach a second temperature at a second heating setting, the temperature-controlled device 2400 can reach a third temperature at a third heating setting, etc.), where the heating settings can be reached by pressing the second button 2682 one or more times.

In some aspects, the display 2676 can comprise the light arrangement 2642, which is similar to the light arrangement 2690 of FIG. 26A in that the light arrangement 2642 can indicate a mode and/or setting of the temperature-controlled device 2400. For example, in some aspects the light arrangement 2642 can comprise lights that can emit a first color when the heating mode is selected and a second color when the cooling mode is selected. As another example, in some aspects the light arrangement 2642 can comprise two or more lights, and a number of lights illuminated can correspond to the selected temperature setting. In some aspects, the light arrangement 2642 may include a light that indicates a charging status or battery level of the battery located in the housing 2402. In some aspects, the light arrangement 2642 may include a light that indicates when the temperature-controlled device 2400 has been turned on by the first button 2680 or the second buttons 2682.

In some aspects, the display 2638 or the display 2676 can be a touchscreen display such that the features described above can be present on the touchscreen. In some aspects, the light arrangement 2642 and the light arrangement 2690 can be supplemented by one or more lights disposed near the heat sink 2418. For example, the light arrangement 2642 and the light arrangement 2690 can comprise additional lights arranged around an inner diameter of the housing 2402 near the second end 2406. In some aspects, the additional lights can comprise the indicator 2590. In some aspects, the light arrangement 2642 and the light arrangement 2690 can comprise additional lights arranged around an inner diameter of the heat spreader 2420 near the bottom surface 2522. In some aspects, the additional lights may be arranged within the housing 2402 on a printed circuit board or PCB, and emission of the light from the additional lights may be visible to the user through the fins of the heat sink 2418 and the vents of the air inlet 2412. When the lights of the light arrangement 2642 are illuminated, the heat sink 2418 can be illuminated by a color that corresponds to the mode selected by the user (e.g., the heating mode, the cooling mode, etc.).

Figure 27:
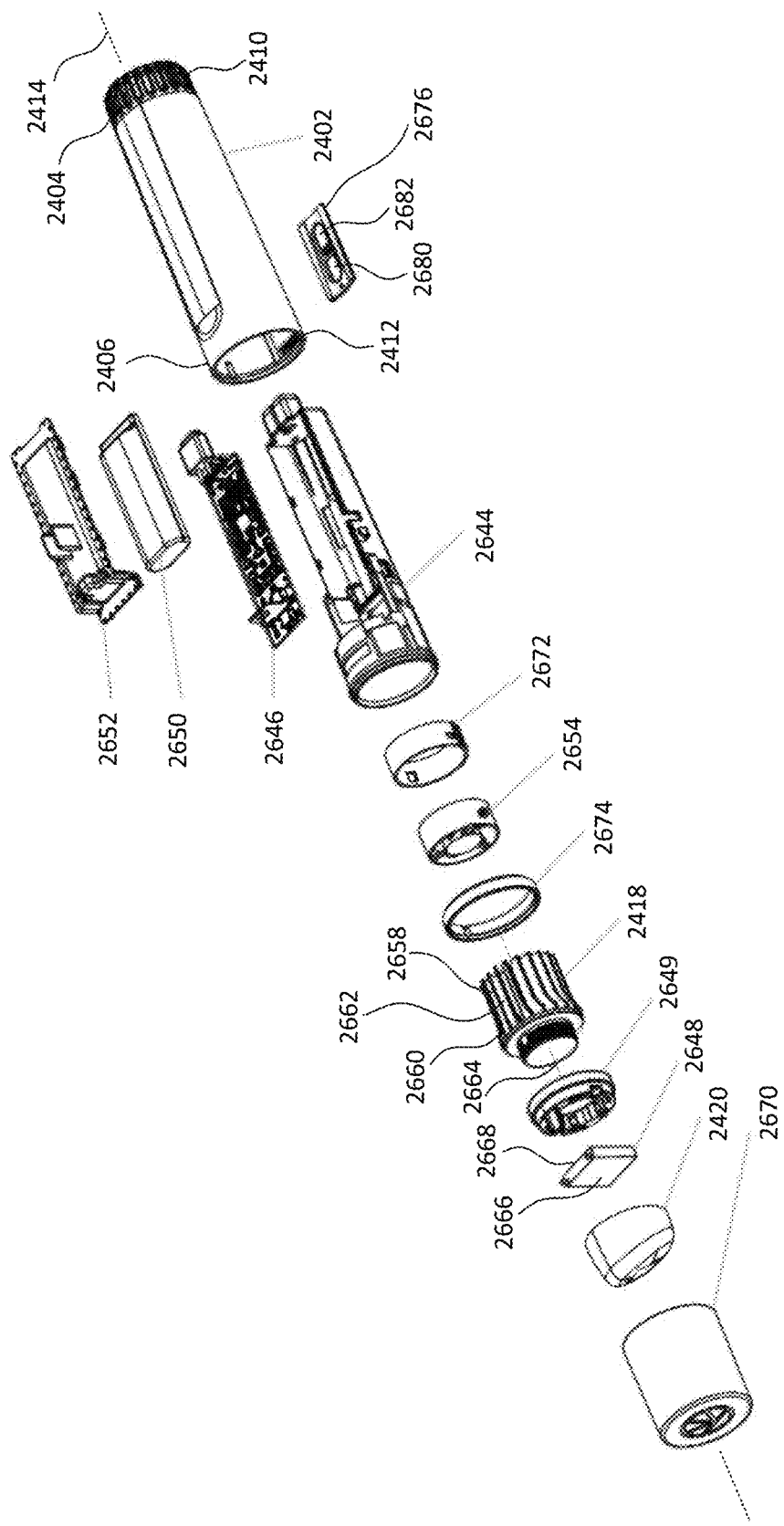
FIG. 27 is an exploded perspective view of the portable therapeutic temperature-controlled device of FIG. 24 according to aspects of the present disclosure.

FIG. 27 is an exploded perspective view of the temperature-controlled device 2400 according to aspects of the present disclosure. In some aspects, the housing 2402 can be configured to receive a support member 2644 such that the support member 2644 can be located in the housing 2402. The support member 2644 can be configured to support one or more structures of the temperature-controlled device 2400. For example, a printed circuit board or PCB 2646 can be disposed in, and be supported by, the support member 2644. The PCB 2646 can be used for electrical and data communication between components. In some aspects, the PCB 2646 can comprise a control unit (e.g., a temperature controller) to communicate with a controllable temperature element 2648 to control various functions such as heating, cooling, or turning the temperature-controlled device 2400 on or off. Thus, in some aspects the PCB 2646 can be configured to selectively control a heating mode and a cooling mode of the controllable temperature element 2648. In some aspects, the PCB 2646 can comprise the light arrangement 2642 or the light arrangement 2690. In some aspects, the light arrangement 2642 or the light arrangement 2690 can comprise one or more light emitting diodes (LEDs). In some aspects, the PCB 2646 can comprise one or more LEDs of the indicator 2590. Thus, in some aspects, the display 2638 or the display 2676 can be electrically coupled to the PCB 2646 such that the PCB 2646 can control the display 2638 or the display 2676.

In some aspects, the PCB 2646 can be powered by a battery 2650. The battery 2650 can be disposed on the PCB 2646 and can be secured to the PCB 2646 by a cover 2652 configured to connect to the PCB 2646. In some aspects, the battery 2650 can be a disposable battery. In some aspects, the battery 2650 can be a rechargeable battery that can be charged when the temperature-controlled device 2400 is connected to a charger through a charging port in the housing 2402 or when the temperature-controlled device 2400 is placed in the battery charger 2416. In some aspects, the PCB 2646 can comprise a first electrical contact that extends to an outer surface of the housing 2402 to contact an electrical contact on the battery charger 2416. In some aspects, the PCB 2646 can comprise components that allow the battery 2650 to be charged wirelessly, and the battery charger 2416 can be a wireless charger. For example, the PCB 2646 can comprise a wire coil electrically coupled to the battery 2650, and when the wire coil is in proximity to a corresponding wire coil of the battery charger 2416, the battery 2650 can charge wirelessly. Such an arrangement can eliminate the presence of electrical contacts on surfaces of the temperature-controlled device 2400, thereby permitting a display arrangement such as that described with reference to FIGS. 26A-26B.

In some aspects, the PCB 2646 can comprise a coating to protect components on the PCB 2646. For example, the PCB 2646 can comprise a conformal coating that is applied to the PCB 2646 (e.g., sprayed, dipped, potted, etc.) to encapsulate the PCB 2646 and protect the components. The conformal coating can comprise an acrylic, a silicone, a polyurethane, an epoxy, or a combination thereof. As another example, the components of the PCB 2646 can be encapsulated by an overmolding process. As yet another example, the PCB 2646 can comprise a thermal compound configured for heat management (e.g., heat dissipation) of the components.

In some aspects, the temperature-controlled device 2400 can comprise a fan 2654 disposed within the support member 2644. For example, the support member 2644 can comprise a recess sized to receive and support the fan 2654 such that the fan 2654 can be located within the housing 2402. In some aspects, the PCB 2646 can be located between the fan 2654 and the first end 2404 of the housing 2402 along the longitudinal axis 2414. Stated differently, the fan 2654 can be located closer to the second end 2406 of the housing 2402 than the first end 2404 of the housing 2402. In some aspects, the fan 2654 can be configured to draw air into the air inlet 2412 and to push air out of the air outlet 2410. In some aspects, the location of the air inlet 2412 and the air outlet 2410 and the direction of air flow from the air inlet 2412 at the second end 2406 to the air outlet 2410 at the first end 2404 may prevent air from flowing into a user's facial region (e.g., into a user's eyes) during operation of the temperature-controlled device 2400.

In some aspects, the fan 2654 can be in contact with a shock absorber 2672. In some aspects, the shock absorber 2672 can at least partially surround the fan 2654. The shock absorber 2672 can be configured to absorb and/or dissipate at least some of the vibrations that can be generated by the fan 2654.

In some aspects, the temperature-controlled device 2400 can comprise a heat sink 2418 in thermal communication with the fan 2654. In some aspects, the heat sink 2418 can be disposed adjacent to the fan 2654 and aligned with the fan 2654 along the longitudinal axis 2414. In some aspects, the fan 2654 can be located between the heat sink 2418 and the first end 2404 of the housing 2402 along the longitudinal axis 2414. Stated differently, the heat sink 2418 can be located further from the first end 2404 of the housing 2402 than the fan 2654. In some aspects, the heat sink 2418 can be in physical contact with the fan 2654. In some aspects, the heat sink 2418 can be spaced apart from the fan 2654. In some aspects, a portion of the heat sink 2418 can be located within the housing 2402 and a portion of the heat sink 2418 can be located outside of the housing 2402. For example, the heat sink 2418 can comprise a first portion 2658 and a second portion 2660. The first portion 2658 can be located adjacent to the fan 2654 and can be located within the housing 2402 such that the first portion 2658 cannot be viewed by the user. The first portion 2658 can be located between the fan 2654 and the second portion 2660 such that the second portion 2660 is located further from the fan 2654 than the first portion 2658 along the longitudinal axis 2414. In some aspects, the second portion 2660 can be located outside the housing 2402 such that the second portion 2660 can be viewed by the user.

In some aspects, the heat sink 2418 can operate in a manner similar to the heat sink 132. For example, the heat sink 2418 can be configured to pull heat from the controllable temperature element 2648, and the fan 2654 can direct the heat away from the heat sink 2418 and the other components. To pull the heat from the controllable temperature element 2648, the heat sink 2418 can comprise fins 2662 that draw the heat from the controllable temperature element 2648. The fins 2662 can extend radially outward from a heat sink axis 2664 that is coaxial with the longitudinal axis 2414. Thus, in some aspects the heat sink 2418 can comprise a circular cross section. In some aspects, the air inlet 2412 can circumferentially surround the first portion 2658 of the heat sink 2418 such that the air flowing past the fins 2662 (as directed by the fan 2654) can direct heat away from the heat sink 2418 and out vents of the air outlet 2410.

In some aspects, the controllable temperature element 2648 can be in thermal communication with the heat sink 2418 and can be configured to generate heating and cooling. In some aspects, the controllable temperature element 2648 can be similar to the controllable temperature element 134 in its function, though the controllable temperature element 2648 can comprise a different size and/or shape than the controllable temperature element 134 to fit within the temperature-controlled device 2400.

In some aspects, the controllable temperature element 2648 can be located between the heat spreader 2420 and the heat sink 2418 along the longitudinal axis 2414. In some aspects, the controllable temperature element 2648 can be aligned with the heat sink 2418 along the longitudinal axis 2414 and/or the heat sink axis 2664. In some aspects, the heat sink 2418 can be located between the controllable temperature element 2648 and the fan 2654 along the longitudinal axis 2414. In some aspects, the controllable temperature element 2648 can be located further from the first end 2404 of the housing 2402 than the heat sink 2418. In some aspects, the controllable temperature element 2648 can be located outside of the housing 2402. Thus, the air inlet 2412 can be located below the controllable temperature element 2648 and above the air outlet 2410.

In some aspects, the controllable temperature element 2648 can comprise a first surface 2666 located opposite a second surface 2668, and the second surface 2668 can be disposed adjacent to the second portion 2660 of the heat sink 2418. In some aspects, the second surface 2668 can be in contact with the second portion 2660 of the heat sink 2418. In some aspects, the second surface 2668 can be spaced apart from the second portion 2660 of the heat sink 2418 and can be in thermal communication with the second portion 2660 of the heat sink 2418. The first surface 2666 can be disposed adjacent to the bottom surface 2522 of the heat spreader 2420. In some aspects, the bottom surface 2522 can be in contact with the first surface 2666. In some aspects, the bottom surface 2522 can be spaced apart from the first surface 2666 and can be in thermal communication with the first surface 2666.

In some aspects, the controllable temperature element 2648 can be aligned with the heat spreader 2420 along the longitudinal axis 2414 such that the controllable temperature element 2648 is located between the heat spreader 2420 and the heat sink 2418 along the longitudinal axis 2414. In some aspects, a spreader holder element 2649 may be configured to hold the controllable temperature element 2648 and the heat spreader 2420 in place. The spreader holder element 2649 may be coupled to the second portion 2660 of the heat sink 2418, and the controllable temperature element 2648 and heat spreader 2420 may be mounted on or positioned in the spreader holder element 2649. In some aspects, the spreader holder element 2649 may comprise a plastic material.

In some aspects, the PCB 2646 can control the controllable temperature element 2648 for heating and cooling. For example, the user can select a heating mode or a cooling mode on the display 2638 or the display 2676. Selecting the heating mode or the cooling mode can cause the PCB 2646 to communicate with the controllable temperature element 2648 to cause the controllable temperature element 2648 to change its temperature. In some aspects, when the heating mode is selected, the controllable temperature element 2648 can reach a temperature of greater than or equal to 30 degrees Celsius and less than or equal to 50 degrees Celsius. In some aspects, when the heating mode is selected, the controllable temperature element 2648 can reach a temperature of greater than or equal to 35 degrees Celsius and less than or equal to 43 degrees Celsius. In some aspects, when the heating mode is selected, the controllable temperature element 2648 can reach a temperature of greater than or equal to 40 degrees Celsius and less than or equal to 42 degrees Celsius. In some aspects, when the cooling mode is selected, the controllable temperature element 2648 can reach a temperature of greater than or equal to 6 degrees Celsius and less than or equal to 18 degrees Celsius. In some aspects, when the cooling mode is selected, the controllable temperature element 2648 can reach a temperature of greater than or equal to 8 degrees Celsius and less than or equal to 16 degrees Celsius. In some aspects, when the cooling mode is selected, the controllable temperature element 2648 can reach a temperature of greater than or equal to 10 degrees Celsius and less than or equal to 14 degrees Celsius.

In some aspects, the surfaces of the heat spreader 2420 (for example, the top surface 2524 and the outer surface 2526) can reach approximately the same temperature as the controllable temperature element 2648 when in the heating mode and the cooling mode. Thus, a user can manipulate and maneuver the temperature-controlled device 2400 to various orientations relative to the face of the user to position the heat spreader 2420 against the face of the user for the desired heating and cooling effects.

In some aspects, a ring 2674 can be coupled to the housing 2402 or the heat spreader 2420. The ring 2674 can be a decorative component for aesthetic purposes and can cover portions of the temperature-controlled device 2400 that may be less aesthetically pleasing.

In some aspects the temperature-controlled device 2400 can comprise a cap 2670 configured to interface with the housing 2402 to enclose the heat spreader 2420 and the heat sink 2418 when the temperature-controlled device 2400 is not in use. In some embodiments, cap 2670 can interface with the housing 2402 through a snap-fit connection.

In some aspects, the arrangement of the components of the temperature-controlled device 2400 can be modified for purposes of manufacturing efficiency and/or cost control. For example, the relative positions of components such as the PCB 2646, the battery 2650, the fan 2654, the heat sink 2418, etc., can be changed to reduce assembly time, increase assembly efficiency, increase first pass yield, reduce manufacturing scrap, etc. Increasing efficiency of manufacturing can include reducing soldered connections for electrical components. For example, connections between the PCB 2646 and the fan 2654, the battery 2650, etc., can be made using electrical connectors instead of soldered connections, thereby reducing assembly time.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Aspects using the singular or plural number may also include the plural or singular number respectively. The word "or" in reference to a list of two or more items, covers all of the following interpretations of the word: any of the items in the list, all of the items in the list, and any combination of the items in the list.

The above-detailed description of aspects of the disclosure is not intended to be exhaustive or to limit the teachings to the precise form disclosed above. While specific aspects of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another aspect, instructions or sub-operations of distinct operations may be implemented in an intermittent and/or alternating manner.

The teachings of the disclosure provided herein can be applied to other systems, not necessarily the system described above. The elements and acts of the various aspects described above can be combined to provide further aspects. Any measurements or dimensions described or used herein are merely exemplary and not a limitation on the present disclosure. Other measurements or dimensions are within the scope of the disclosure.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further aspects of the disclosure.

These and other changes can be made to the disclosure in light of the above Detailed Description of the Aspects. While the above description describes certain aspects of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific aspects disclosed in the specification unless the above Detailed Description of the Aspects section explicitly defines such terms. Accordingly, the actual scope of the disclosure encompasses not only the disclosed aspects, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary aspects of the disclosure have been shown and described, it is to be understood that all the terms used herein are descriptive rather than limiting, and that many changes, modifications, and substitutions may be made by one having ordinary skill in the art without departing from the spirit and scope of the disclosure.

What is claimed is:

1. A portable temperature controlled device comprising:
   a cylindrical housing comprising an air inlet and an air outlet in fluid communication with each other, wherein the air inlet is configured to permit air to flow into the cylindrical housing and the air outlet is configured to permit the air to flow out of the cylindrical housing;
   a fan located within the cylindrical housing;
   a heat sink disposed adjacent to the fan, wherein a first portion of the heat sink is located within the cylindrical housing and a second portion of the heat sink is located outside of the cylindrical housing, wherein the second portion extends entirely around a longitudinal axis of the cylindrical housing;
   a controllable temperature element comprising a first surface located opposite a second surface, the controllable temperature element configured to generate heating and cooling, wherein the second surface of the controllable temperature element is disposed adjacent to the second portion of the heat sink;
   a heat spreader comprising a bottom surface located opposite a top surface, wherein the bottom surface is disposed adjacent to the first surface of the controllable temperature element and the top surface is configured to contact a face of a user, wherein the top surface is oriented at a non-zero angle relative to the bottom surface; and
   a temperature controller connected to the controllable temperature element.

2. The portable temperature controlled device of claim 1, further comprising a support member located in the cylindrical housing and configured to support the fan.

3. The portable temperature controlled device of claim 1, further comprising a printed circuit board located within the cylindrical housing and in electrical communication with the temperature controller, wherein the printed circuit board is configured to selectively control a heating mode and a cooling mode of the temperature controller.

4. The portable temperature controlled device of claim 3, wherein selecting the heating mode causes the controllable temperature element to reach a temperature of greater than or equal to 35 degrees Celsius and less than or equal to 43 degrees Celsius, and selecting the cooling mode causes the controllable temperature element to reach a temperature of greater than or equal to 8 degrees Celsius and less than or equal to 16 degrees Celsius.

5. The portable temperature controlled device of claim 3, wherein the printed circuit board comprises a first electrical contact that extends to an outer surface of the cylindrical housing, the first electrical contact configured to contact a second electrical contact of a battery charger to charge a battery located in the cylindrical housing.

6. The portable temperature controlled device of claim 3, wherein the printed circuit board comprises a light emitting diode configured to emit a first light when the heating mode is selected and a second light when the cooling mode is selected, wherein a color of the first light is different from a color of the second light.

7. The portable temperature controlled device of claim 1, wherein the air inlet is located below the controllable temperature element and above the air outlet.

8. The portable temperature controlled device of claim 1, wherein the heat spreader is configured to receive thermal energy from the controllable temperature element.

9. The portable temperature controlled device of claim 1, wherein the top surface of the heat spreader is oriented at an angle of greater than or equal to 10 degrees and less than or equal to 45 degrees relative to the bottom surface of the heat spreader.

10. The portable temperature controlled device of claim 9, wherein when the top surface of the heat spreader is in contact with a surface of the face of the user, a longitudinal axis of the cylindrical housing is oriented at angle of greater than or equal to 10 degrees and less than or equal to 45 degrees relative to the surface of the face of the user.

11. A portable temperature controlled device comprising:
a cylindrical housing comprising a first end located opposite a second end and defining a longitudinal axis extending between the first end and the second end, the second end comprising an air inlet, the first end comprising an air outlet and configured to receive a support member;
a fan disposed within the support member, the fan being located closer to the second end of the cylindrical housing than the first end of the cylindrical housing;
a heat sink aligned with the fan along the longitudinal axis, the heat sink being located further from the first end of the cylindrical housing than the fan;
a controllable temperature element aligned with the heat sink along the longitudinal axis, the controllable temperature element configured to generate heating and cooling, wherein the heat sink is located between the controllable temperature element and the fan; and
a heat spreader aligned with the controllable temperature element along the longitudinal axis and located outside of the cylindrical housing, wherein the controllable temperature element is located between the heat spreader and the heat sink, wherein the heat spreader comprises a contact surface configured to contact a face of a user, the contact surface being oriented at a non-zero angle relative to the first end of the cylindrical housing.

12. The portable temperature controlled device of claim 11, wherein the heat sink comprises fins extending radially outward from a heat sink axis that is coaxial with the longitudinal axis, wherein the heat sink comprises a circular cross-section.

13. The portable temperature controlled device of claim 11, wherein the heat spreader is configured to receive thermal energy from the controllable temperature element.

14. The portable temperature controlled device of claim 11, wherein the fan is configured to draw air into the air inlet and to push air out of the air outlet.

15. The portable temperature controlled device of claim 14, wherein the air inlet circumferentially surrounds at least a portion of the heat sink.

16. The portable temperature controlled device of claim 11, wherein the contact surface of the heat spreader is oriented at an angle of greater than or equal to 10 degrees and less than or equal to 45 degrees relative to the second end of the cylindrical housing.

17. The portable temperature controlled device of claim 11, wherein when the contact surface of the heat spreader is in contact with a surface of the face of the user, the longitudinal axis is oriented at an angle of greater than or equal to 10 degrees and less than or equal to 45 degrees relative to the surface of the face of the user.

18. The portable temperature controlled device of claim 11, further comprising a printed circuit board disposed in the support member, wherein the printed circuit board is located between the fan and the first end of the cylindrical housing along the longitudinal axis, wherein the printed circuit board is configured to selectively control a heating mode and a cooling mode of the controllable temperature element.

19. The portable temperature controlled device of claim 18, wherein selecting the heating mode causes the controllable temperature element to reach a temperature of greater than or equal to 35 degrees Celsius and less than or equal to 43 degrees Celsius, and selecting the cooling mode causes the controllable temperature element to reach a temperature of greater than or equal to 8 degrees Celsius and less than or equal to 16 degrees Celsius.

20. The portable temperature controlled device of claim 18, wherein the printed circuit board comprises a light emitting diode configured to emit a first light when the heating mode is selected and a second light when the cooling mode is selected, wherein a color of the first light is different from a color of the second light.

21. A portable temperature controlled device comprising:
a cylindrical housing;
a fan disposed within the cylindrical housing;
a heat sink in thermal communication with the fan;
a controllable temperature element in thermal communication with the heat sink and configured to generate heating and cooling; and
a heat spreader in thermal communication with the controllable temperature element, the heat spreader configured to increase in temperature when the controllable temperature element generates heating and configured to decrease in temperature when the controllable temperature element generates cooling, the heat spreader comprising:
a bottom surface;
a top surface; and
an outer surface extending between the bottom surface and the top surface;
wherein a temperature of the top surface is approximately equal to a temperature of the outer surface when the controllable temperature element generates heating and cooling.

22. The portable temperature controlled device of claim 21, wherein the heat spreader comprises a bottom surface comprising a circular shape and the outer surface extends between the bottom surface and the top surface at an acute angle relative to the bottom surface.

23. The portable temperature controlled device of claim 22, wherein the top surface is oriented at a nonzero angle relative to the bottom surface.

24. The portable temperature controlled device of claim 23, wherein the top surface and the outer surface meet at a transition region, wherein the transition region comprises a first radius of curvature where an uppermost portion of the top surface meets the outer surface and the transition region comprises a second radius of curvature where a remainder of the top surface meets the outer surface, wherein the second radius of curvature is greater than the first radius of curvature.

* * * * *